United States Patent
Atzrodt et al.

(10) Patent No.: US 9,340,489 B2
(45) Date of Patent: May 17, 2016

(54) PROCESS FOR THE PREPARATION OF DEUTERATED COMPOUNDS CONTAINING N-ALKYL GROUPS

(75) Inventors: Jens Atzrodt, Frankfurt am Main (DE); Volker Derdau, Frankfurt am Main (DE); Wolfgang Holla, Frankfurt am Main (DE); Matthias Beller, Ostseebad Nienhagen (DE); Lorenz Neubert, Rostock (DE); Dirk Michalik, Rostock (DE)

(73) Assignee: SANOFI, Paris (FR)

( * ) Notice: Subject to any disclaimer, the term of this patent is extended or adjusted under 35 U.S.C. 154(b) by 98 days.

(21) Appl. No.: 14/118,705

(22) PCT Filed: May 21, 2012

(86) PCT No.: PCT/EP2012/059344
§ 371 (c)(1),
(2), (4) Date: Nov. 19, 2013

(87) PCT Pub. No.: WO2012/160015
PCT Pub. Date: Nov. 29, 2012

(65) Prior Publication Data
US 2014/0081019 A1    Mar. 20, 2014

(30) Foreign Application Priority Data
May 23, 2011 (EP) .................................. 11305634

(51) Int. Cl.
| C07C 217/28 | (2006.01) |
| C07B 59/00  | (2006.01) |
| C07C 211/07 | (2006.01) |
| C07C 211/08 | (2006.01) |
| C07C 211/27 | (2006.01) |
| C07D 207/06 | (2006.01) |
| C07D 211/14 | (2006.01) |
| C07D 223/04 | (2006.01) |
| C07D 241/04 | (2006.01) |
| C07D 401/04 | (2006.01) |

(52) U.S. Cl.
CPC ............... *C07C 217/28* (2013.01); *C07B 59/00* (2013.01); *C07C 211/07* (2013.01); *C07C 211/08* (2013.01); *C07C 211/27* (2013.01); *C07D 207/06* (2013.01); *C07D 211/14* (2013.01); *C07D 223/04* (2013.01); *C07D 241/04* (2013.01); *C07D 401/04* (2013.01)

(58) Field of Classification Search
None
See application file for complete search history.

(56) References Cited

U.S. PATENT DOCUMENTS

| 5,075,337 A | 12/1991 | Cordi et al. |
| 5,167,948 A | 12/1992 | Wenzel |
| 5,846,514 A | 12/1998 | Foster et al. |
| 2010/0143287 A1 | 6/2010 | Gant |

FOREIGN PATENT DOCUMENTS

| EP | 1 707 548 A1 | 10/2006 |
| WO | 2008122010 A1 | 10/2008 |
| WO | 2009005069 A1 | 8/2009 |

OTHER PUBLICATIONS

Casey, C.P. et al., Hydrogen Transfer to Carbonyls and Imines from a Hydroxycyclopentadienyl Ruthenium Hydride: Evidence for Concerted Hydride and Proton Transfer, J. Am. Chem. Soc., (2001), vol. 123, pp. 1090-1100.
Garrido, E. M. et al., Fluoxetine and Norfluoxetine Revisited: New Insights into the Electrochemical and Spectroscopic Properties, J. Phys. Chem. A, (2009), vol. 113, pp. 9934-9944.
Lockley, W.J.S. et al., Rhodium- and ruthenium-catalysed hydrogen isotope exchange, J. Label Compd. Radiopharm, (2010), vol. 53, pp. 704-715.
International Search Report dated Aug. 8, 2012 issued in PCT/EP2012/059344.
Japanese Office Action dated Nov. 17, 2015, issued in corresponding Japanese Patent Appin. No. 2014-511830.

*Primary Examiner* — Clinton Brooks
*Assistant Examiner* — Jennifer C Sawyer
(74) *Attorney, Agent, or Firm* — Scully Scott Murphy and Presser

(57) ABSTRACT

The present invention relates to a process for deuteration of amines in the alpha and/or beta position of the N-atom by using a deuterium source and a Ruthenium(II) based catalyst.

19 Claims, No Drawings

PROCESS FOR THE PREPARATION OF DEUTERATED COMPOUNDS CONTAINING N-ALKYL GROUPS

The present invention relates to a process for introducing in a compound deuterium in the alpha and/or beta position of an alkyl like residue bonded to a nitrogen atom.

The synthesis of deuterium labelled organic compounds is of fast-growing interest due to the widespread application of mass spectrometry as a specific detection and investigation tool in pharmacological, chemical and environmental research.

For example, deuterated organic compounds are widely used as internal standards in pharmaceutical drug development for the investigation of samples originating from environmental, animal and human studies. For a quantitative LC-MS/MS analysis of new drug candidates or relevant metabolites in complex matrices (like blood, urine, bile etc.), stable isotopically labelled internal standards are considered essential in order to avoid matrix effects, such as ion suppression or ion enhancement. Similar applications of internal MS standards are mandatory for toxin and food analysis as well as the designation of origin of food ingredients.

Another important application of deuterated compounds is based on the property of deuterium to form stronger bonds with other atoms compared to hydrogen which are therefore more difficult to cleave both chemically and metabolically. That means selective incorporation of deuterium at the site of initial metabolic oxidation may slow down the metabolism of a drug and could reduce the formation of unwanted metabolites. A further consequence of blocking major metabolic pathways can be a lower clearance of the drug and hence a longer residence time and enhanced efficacy. Therefore, the deuteration approach can potentially lead to a variety of beneficial effects, including longer duration of action, improved safety profile and reduced levels of toxic metabolites.

In addition to deuterated organic molecules, also tritium labelled compounds are widely employed for metabolic and pharmacokinetic investigations of new drug candidates.

Compared with a conventional synthesis starting from a suitable commercially available stable labelled precursor, H/D (hydrogen/deuterium) exchange (HDE) can be a cost- and time-efficient alternative approach particularly if it has to be carried out directly on the target molecule or an advanced intermediate. Comprehensive reviews on existing HDE methods have been published recently (Atzrodt et al., Angew. Chem. Int. Ed. 2007, 46, 7744-7765; Junk et al., J. Chem. Soc. Rev. 1997, 26, 401-406). The known methods for HDE can be divided into three different categories: 1) pH-dependent (acidic/basic); 2) heterogeneous metal catalyzed; and 3) homogeneous metal catalyzed. Ruthenium is one of the various metals, which has been utilized for both homogeneous and heterogeneous HDE reactions.

For nitrogen compounds heterogeneous ruthenium catalyzed HDE was effective for the regiospecific deuteration of aliphatic primary and secondary amines at the alpha-position to the amine-nitrogen employing Ru/C (WO2009/005069A1, Wako Pure Chem. Industries). The reaction proceeds highly regio- and chemoselectively at the alpha-position, however hydrogens in the beta position are not or only unspecifically accessible for HDE. Another heterogeneous HDE method utilizes Pd/C as the catalyst for the deuteration of N-heteroaromatic compounds such as substituted indoles, pyridines and imidazoles as described in EP1561741A1 (Wako Pure Chem. Industries).

Existing methods for homogeneous ruthenium catalyzed HDE mainly apply $Ru(PPh_3)_3Cl_2$ as catalyst with $D_2O$ as deuterium source. Selective deuteration of the alpha-position of primary alcohols and primary and secondary amines is described in Takahashi et al. Chem. Lett. 2005, 34, 192-193. The reaction required high temperatures up to 185° C. and high pressures of up to 10 atm. Secondary alcohols and tertiary amines haven't been successfully applied. With trihexylamine a small amount of HDE in the alpha position was observed only.

Basically, existing methods for HDE of nitrogen containing compounds often require strong reaction conditions, very long reaction times and the alpha and beta selectivity relative to the nitrogen is usually low. Thus, there still remains the need to develop a suitable process for an efficient and selective deuteration of compounds containing nitrogen functionalities as these are common structural elements in many active pharmaceutically drugs. Alpha and beta positions of aliphatic amino groups are of particular interest for deuteration due to their metabolic reactivity and the opportunity to selectively prepare internal MS standards with a sufficient mass difference compared to the unlabelled analogue.

Definitions

The terms $(C_1-C_{12})$alkyl or $(C_1-C_{12})$alkylene are understood as a hydrocarbon residue which can be linear, i.e. straight-chain, or branched and has 1, 2, 3, 4, 5, 6, 7, 8, 9, 10, 11 or 12 carbon atoms, respectively. This also applies if an alkyl group occurs as a substituent on another group, for example in an alkoxy group (O-alkyl), a thio group (S-alkyl) or a —$O(CH_2)_n$—O— group, an alkoxycarbonyl group or an arylalkyl group. Examples of alkyl groups are methyl, ethyl, propyl, butyl, pentyl or hexyl and branched groups such as isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. Examples of alkylene groups are methylene, ethylene, propylene, butylene and the like.

One or more hydrogen atoms may be substituted by halogen, especially fluorine, atoms, i.e. alkyl groups may be fluorinated, e.g. perfluorinated. Examples of fluorinated alkyl groups are $CF_3$, $CH_2CHF_2$, $CH_2CF_3$, $OCF_3$, or S—$CF_3$.

$(C_1-C_6)$Alkenyl are, for example, vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl. An alkenyl wherein one carbon atom has a double bond to another carbon which is part of a ring, such as methenyl (—HC═C(C is part of a ring, e.g. cyclohexan), is included in this definition.

$(C_2-C_6)$Alkynyl are alkyl groups containing at least one triple bond such as, for example, in ethynyl, 1-propynyl, 2-propynyl (=propargyl) or 2-butynyl.

$(C_3-C_{10})$cycloalkyl groups are mono or bicyclic alkyl groups containing 3, 4, 5, 6, 7, 8, 9 or 10 ring carbon atoms like cyclopropyl, cyclobutyl, cyclopentyl, cyclohexyl or cyclooctyl, which can also be substituted and/or unsaturated. Cycloalkyl groups can be saturated or partly unsaturated, especially when an alkyl group is condensed to an aryl group. For example a cycloalkyl radical may contain none, one or two double bonds. Examples of such unsaturated groups are cyclopentenyl, cyclohexenyl, tetrahydronaphthyl, alpha- or beta-tetralon-, indanyl- or indan-1-on-yl. A cycloalkyl group may further by fused to one or two phenyl rings such as in dibenzo[a,d]cyclohepten.

This also applies if they carry substituents or occur as substituents of other residues, for example in cycloalkylalkyl. Cycloalkyl groups can be bonded via any carbon atom. Substituted cycloalkyl radicals may be substituted in identical or different positions.

A $(C_6-C_{10})$aryl group means an aromatic ring or a ring system which comprises two aromatic carbon rings which are fused or otherwise linked, for example a phenyl, naphthyl, or biphenyl. Phenyl is a preferred $(C_6-C_{10})$aryl group.

In monosubstituted phenyl groups the substituent can be located in the 2-position, the 3-position or the 4-position, with the 3-position and the 4-position being preferred. If a phenyl group carries two substituents, they can be located in 2,3- position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position.

The above statements relating to phenyl groups correspondingly apply to divalent groups derived from phenyl groups, i.e. phenylene which can be unsubstituted or substituted 1,2-phenylene, 1,3-phenylene or 1,4-phenylene. The above statements also correspondingly apply to the aryl subgroup in arylalkylene groups. Examples of arylalkylene groups which can also be unsubstituted or substituted in the aryl subgroup as well as in the alkylene subgroup, are benzyl, 1-phenylethylene, 2-phenylethylene, 3-phenylpropylene, 4-phenylbutylene, 1-methyl-3-phenyl-propylene.

The term $(C_3-C_{15})$heterocycloalkyl refers to substituted and unsubstituted non-aromatic 3 to 7 membered monocyclic groups, 7 to 11 membered bicyclic groups, and 10 to 15 membered tricyclic groups which have at least one heteroatom (O, S or N) in at least one of the rings. Each ring of the $(C_3-C_{15})$heterocycloalkyl group containing a heteroatom can contain one or two oxygen or sulfur atoms and/or from one to four nitrogen atoms, provided that the total number of heteroatoms in each ring is four or less, and further provided that the ring contains at least one carbon atom. For example, a $C_6$-heterocycloalkyl may contain 5 carbon atoms and 1 nitrogen atom as is the case of piperidinyl. The fused rings completing the bicyclic and tricyclic groups may contain only carbon atoms and may be saturated, partially saturated, or unsaturated (aromatic). A heterocycloalkyl group comprises saturated, partly unsaturated, mixed aromatic/saturated and mixed aromatic/partly unsaturated rings.

Examples for such mixed groups are 2,3-Dihydro-benzo[1,4]dioxine or 2,2,6-trimethyl-chromane.

The nitrogen and sulfur atoms may optionally be oxidized and the nitrogen atoms may optionally be quaternized. The $(C_3-C_{15})$heterocycloalkyl group may be attached at any available nitrogen or carbon atom.

Heterocycloalkyl residues may be unsubstituted or be substituted one, two, three or four times, preferably one, two or three times, by identical or different residues in identical or different positions. Substitution can occur on free carbon atoms or on nitrogen atoms.

Examples of monocyclic groups are oxiranyl, aziridinyl, tetrahydrofuranyl, tetrahydropyranyl, dioxolanyl, for example 1,3-dioxolane, dioxanyl, for example 1,4-dioxanyl, oxetanyl, piperidinyl, pyrrolidinyl, imidazolidinyl, triazolidinyl, hexahydropyrimidinyl, piperazinyl, tetrahydropyridazinyl, triazinane, for example, 1,3,5-triazinanyl, 1,2,3-triazinanyl or 1,2,4-triazinanyl, tetrahydrothiophenyl, tetrahydrothiopyranyl, dithiolane, for example 1,3-dithiolane, dithianyl, thiazolidinyl, oxazolidinyl, oxathiolanyl, for example 1,3-oxathiolanyl, morpholinyl or thiomorpholinyl, diazepanyl, for example 1,4-diazepanyl.

Examples of bicyclic heterocycloalkyl groups include azabicyclo[2.2.2]octyl, indolinyl, isoindolinyl, chromanyl, or quinilizidinyl. An example for a tricyclic heterocycloalkyl is xanthenyl.

Also encompassed are the corresponding ketons (C=O), N-oxides and S-dioxides of these compounds such as 2-oxopiperazinyl, 2-oxopiperidinyl, 2-oxopyrrolidinyl, 2-oxoazepinyl, thiomorpholinyl sulfoxide, thiomorpholinyl sulfone, 1,3-dioxolane and tetrahydro-1,1-dioxothienyl and the like.

$(C_5-C_{15})$Heteroaryl residues are $(C_5-C_6)$monocyclic, $(C_8-C_{10})$bicyclic or tricyclic aromatic ring groups which have at least one heteroatom (O, S or N) in at least one of the rings. One or more ring atoms are oxygen atoms, sulfur atoms and/or nitrogen atoms. A heteroaryl may contain 1, 2, 3 or 4 nitrogen atoms, 1 or 2 oxygen atoms, 1 or 2 sulfur atoms or a combination of various heteroatoms. The heteroaryl residues may be attached by all positions, for example by the 1 position, 2 position, 3 position, 4 position, 5 position, 6 position, 7 position or 8 position and the like.

Examples of $(C_5-C_6)$monocyclic heteroaryl are furyl, thienyl, pyrrolyl, imidazolyl, pyrazolyl, oxazolyl, isoxazolyl, thiazolyl, isothiazolyl, pyridyl, triazolyl, oxadiazolyl, thiadiazolyl, pyrazinyl, pyrimidinyl, pyridazinyl and tetrazolyl.

Examples of bicyclic $(C_8-C_{10})$heteroaryl are benzothiophenyl, benzofuranyl, indolyl, isoindolyl, indazolyl, quinolyl, isoquinolyl, benzimidazolyl, benzothiazolyl, benzoxazolyl, benzotriazolyl, benzoxadiazolyl, benzothiadiazolyl, quinoxalinyl, quinazolinyl, cinnolinyl, phthalazinyl, purinyl, pteridinyl and thienothiazolyl.

Examples of tricyclic heteroaryl groups include carbazolyl, benzindolyl, phenanthrolinyl, acridinyl, phenanthridinyl, phenothiazine and xanthenyl.

Also encompassed are the corresponding N-oxides and S-dioxides of these compounds In one embodiment heteroaryl residues are from the group of monocyclic and bicyclic heteroaryls forming a group of $(C_5-C_{10})$heteroaryl. In one embodiment $(C_5-C_{10})$heteroaryl residues are furyl, thienyl, imidazolyl, pyrazolyl, oxazolyl, isoxazolyl, thiazolyl, pyridyl, triazolyl, oxadiazolyl, pyrazinyl, pyrimidinyl, pyridazinyl, indolyl, benzthiophenyl, quinolyl, benzimidazolyl, benzothiazolyl, benzoxazolyl, benzotriazolyl, and benzoxadiazolyl.

A preferred $(C_5-C_{10})$heteroaryl residue is $(C_5-C_6)$heteroaryl. Preferred $(C_5-C_6)$heteroaryl residues are furyl, thienyl, imidazolyl, pyrazolyl, oxazolyl, isoxazolyl, thiazolyl, pyridyl, triazolyl, oxadiazolyl, pyrazinyl, pyrimidinyl, and pyridazinyl, Preferred examples of $(C_5-C_{10})$heteroaryl residues are 2- or 3-thienyl, 2 or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4 or -5-yl, 1,2,4-oxadiazol-3 or -5-yl, 1,3,4-oxadiazol-2-yl or-5-yl, 2-, 4- or 5-thiazolyl, 3-, 4- or 5-isothiazolyl, 1,3,4-thiadiazol-2 or -5-yl, 1,2,4-thiadiazol-3 or -5-yl, 1,2,3-thiadiazol-4 or -5-yl, 2-, 3- or 4-pyridyl, 2-, 4-, 5- or 6-pyrimidinyl, 3- or 4-pyridazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl.

Enclosed are also the respective n-oxides, for example 1-oxy-2-, -3- or -4-pyridyl. Heteroaryl residues may be unsubstituted or substituted one, two, three or four times, preferably one, two or three times, by identical or different residues.

Halogen means fluoro, chloro, bromo or iodo.

DETAILED DESCRIPTION OF THE INVENTION

It has now been found that within the group of cyclopentadienyl-ruthenium-complexes the so called Shvo-catalyst, which is (1-Hydroxy-tetraphenylcyclopentadienyl-(tetraphenyl-2,4-cyclopentadien-1-one)-µ-hydrotetracarbonyldiruthenium(II) (see formula 1 in FIG. 1 below) or a derivative thereof can be used successfully in a process for H/D exchange in the alpha and/or beta position of an N-atom in a organic compound.

The Shvo catalyst has been described and already used for various purposes (Conley et al. Chem. Rev. 2010, 110, 2294-2312 and Karvembu et al. Coord. Chem. Rev. 2005, 249, 911-918).

The catalyst can be described in its dimeric (1), dehydrogenated (1a) and hydrogenated (1b) monomeric form (FIG. 1), which are all included in the scope of the catalyst. For nomenclature and naming purposes of the catalyst the structure shown in 1 is used.

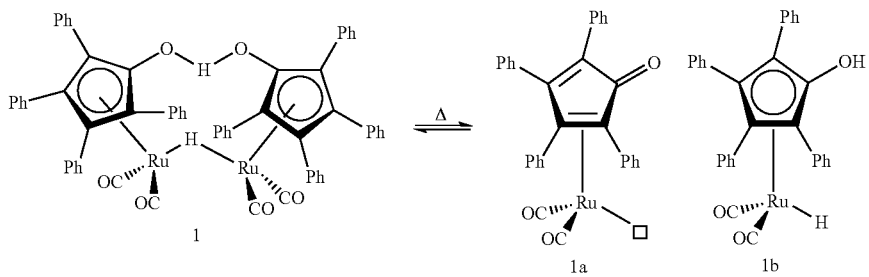

Based on his bimetallic structure containing a hydration as well as a dehydration-component the Shvo catalyst was used in the past for various purposes such in the catalytic oxidation of alcohols (e.g. Csjernijk et al. J. Org. Chem. 2002, 67, 1657-1662) or in the kinetic separation of racemic alcohols (e.g. Verzijl et al. Tetrahedron: Asymmetry 2005, 16, 1603-1610).

More recently the Shvo-catalyst was used for the activation of amines and thus used for the N-alkylation of indols (Bähn et al. Chem. Eur. J. 2010, 16, 3590-3593), for the alkylation of primary amines to prepare secondary amines (Bähn et al. Adv. Synth. Catal. 2008, 350, 2099-2103) and for the selective synthesis of monoalkylated aryl amines (Hollmann et al. Chem. Commun. 2008, 3199-3201; Hollmann et al. Angew. Chem. Int. Ed. 2007, 46, 8291-8294).

The preparation of deuterated compounds using this catalyst has not been described or suggested in any of these publications, especially not of those compounds according to the present invention.

It has been found that the Shvo catalyst can be used in the process of the present invention. Moreover, derivatives of this catalyst which do not affect the general ability to perform the deuteration reaction are included in the scope of the catalyst for use in the process of the present invention.

Accordingly, the Shvo catalyst or a derivative thereof as depicted below in its dimeric precatalytic form (Formula 2) and its disproportionated form (Formula 2a and 2b) having a ruthenium core, 4 moderately bonded ligands (L) (like CO, CN or COD) plus H,cyclopentadiene ligands optionally substituted with four substituents Z independently of each other selected from ($C_1$-$C_6$)alkyl or phenyl, wherein phenyl is optionally substituted one or more times, preferably 1 to 3 times, by halogen, preferably F or Cl, and a group with an oxidative pair (UH/U), like OH/=O, $NHR_5$/C=$NR_5$, wherein $R_5$ is ($C_1$-$C_6$)alkyl, phenyl, benzyl, or is SH/=S) is considered to work in the same manner to initiate a selective H/D exchange.

wherein
UH is OH, NHR5, or SH
U is O, $NR_5$ or S,
$R_5$ is ($C_1$-$C_6$)alkyl, phenyl or —$CH_2$-phenyl,
Z is, independently of each other, ($C_1$-$C_6$)alkyl or phenyl, wherein phenyl is optionally substituted 1 or more times, preferably 1 to 3, times, by halogen, preferably F or Cl, and L is CO, CN or COD,
may be useful as a catalyst in the process of the present invention.

It has now been found that the Shvo catalyst or a derivative thereof can be used in the deuteration of the alpha and/or beta position of a N-atom in a compound containing at least one substituent containing a N—C—C structural element, such as an alkyl or an alkylene group comprising at least 2 carbon atoms bound to the nitrogen such as e.g. ethyl or ethylene.

In one embodiment the present invention relates to a process for the preparation of a deuterated compound (II) containing at least one structural element of the formula N—C—C, which is not part of an aromatic ring system,
and wherein the amount of deuterium at the carbon atom in the alpha position and/or the carbon atom in the beta position of the structural element is at least 1%,
characterized in that a compound (1) comprising a residue which contains at least one structural element N—C—C, wherein at least one H atom is at each carbon atom of the structural element and the N—C—C element is not part of an aromatic ring system, is reacted with a deuterium source in the presence of a catalyst of formula (2)

1-UH-tetra-Z-cyclopentadienyl-(tetra-Z-2,4-cyclopentadien-1-U)-μ-hydro-tetra-L-diruthenium(II)      (2), wherein
UH is OH, $NHR_5$, or SH;
U is O, $NR_5$ or S;

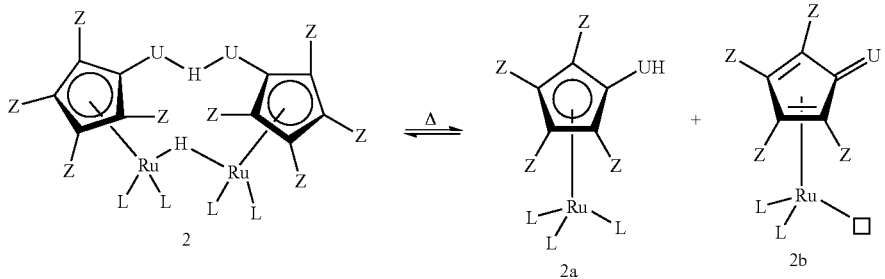

(FIG. 2)
Accordingly, a catalyst of the formula (2)

1-UH-tetra-Z-cyclopentadienyl-(tetra-Z-2,4-cyclopentadienyl-1-U)-μ-hydro-tetra-L-diruthenium(II)      (2), $R_5$ is ($C_1$-$C_6$)alkyl, phenyl, or —$CH_2$-phenyl;
Z is, independently of each other, ($C_1$-$C_6$)alkyl or phenyl, wherein each phenyl is optionally substituted by ($C_1$-$C_6$)alkyl or phenyl, wherein phenyl is optionally substituted 1 or more times, preferably 1 to 3 times, by halogen, preferably F or Cl; and L is CO, CN or COD.

The structural element of the formula N—C—C is hereinafter also referred to as the "structural element". There is no limitation in the structure of a compound (I) which may be used in the process of the present invention. Accordingly, the structure and constitution of a compound which can be deuterated can vary widely. The only requirement is that the compound comprises a residue or substituent which contains at least as said once the structural element and that this element is not directly part of an aromatic ring system. The terms substituent and residue do have the same meaning and are used herein interchangeable. The compound may comprise one or more residues, wherein each residue may contain said structural element at least once.

In the structural element the remaining two more bonds at the N and the two additional bonds at the C atom next (alpha) to the N-atom and the other three additional bonds at the second (beta) carbon are not shown. Besides having at least an H bonded to each C-atom of the structural element (i.e. the structural element is N—CH—CH in compound (I)), the other 1 or 2 substituents bonded to the alpha carbon or the beta carbon, respectively, which are needed for completing an residue containing at least the structural element once, may be, independently of each other, selected from H or any further organic residue, such as alkyl, aryl, cycloalkyl etc. The same applies to the N-atom. The structural element may also be part of a cyclic ring system as described in more detail below.

Of course, other usual conditions, such as being stable under the thermal reaction conditions used, need to be fulfilled as well. Accordingly, the compound can be an amine such as tributylamine, which contains the structural element three times, but the structural element can also be part of a complex polycyclic molecule such as oxycodone shown in Table 1 or be part of a large molecule having various residues linked together as shown in the examples, including, for example, fexofenadine or sunitinib.

In one embodiment the structural element in a compound (I) is N—C(H)$_m$—C(H)$_n$, wherein m is 1 or 2 and n is 1, 2 or 3, preferably n is 1 or 2. In more specific embodiments thereof the structural element in a compound (I) is N—CH—CH, N—CH$_2$—CH, NCH—CH$_2$ or N—CH$_2$—CH$_2$. In a particular embodiment it is N—CH$_2$—CH$_2$.

As indicated there may be only one H at the C-atom next to the N-atom (alpha) and/or at the second C-atom (beta). Examples for such elements are N—CHR—CHH—, N—CHR—CHR or N—CH2—CHR— wherein, by way of illustration, another residue R is shown which may be any residue or part of a residue but not H. Examples are 2-Diethylamino-1-phenyl-propan-1-ol (see Example 15) or 3-(4-fluorophenyl)-1-methylpiperazine (see Example 20).

The structural element may be part of a primary, secondary or tertiary amine and thus may be present once, twice or three times depending on the kind of further substituent at the N atom. For example, in the tertiary amine Phenyl-N((C$_1$-C$_6$)alkyl)$_2$ contains two alkyl groups, thus the structural element is contained twice. Amine groups comprising an N atom bonded to one, two or even three residues containing the structural element may in turn be present one, two or even more times in a molecule and the product may thus be deuterated at different positions in the molecule where said amine groups containing the structural element are present.

In one embodiment the residue comprising the structural element in compound (I) is N(C$_2$-C$_{12}$)alkylene, —NH(C$_2$-C$_{12}$)alkyl, —N((C$_1$-C$_{12}$)alkyl)((C$_2$-C$_{12}$)alkyl), —(C$_2$-C$_{12}$)alkylene-N((C$_1$-C$_{12}$)alkyl)$_2$, —(C$_1$-C$_{12}$)alkylene-N((C$_1$-C$_{12}$)alkyl)((C$_2$-C$_{12}$)alkyl) or (C$_3$-C$_{15}$)heterocycloalkyl.

More specifically, the residue in compound (I) comprising the structural element is —NH(C$_2$-C$_{12}$)alkyl, preferably —NH(C$_2$-C$_6$)alkyl. In another embodiment the residue is —N((C$_1$-C$_{12}$)alkyl)((C$_2$-C$_{12}$)alkyl), preferably —N((C$_1$-C$_6$)alkyl)((C$_2$-C$_6$)alkyl). In another embodiment the residue is —(C$_1$-C$_{12}$)alkylene-N((C$_1$-C$_{12}$)alkyl)((C$_2$-C$_{12}$)alkyl)), preferably —(C$_1$-C$_6$)alkylene-N((C$_1$-C$_6$)alkyl)((C$_2$-C$_6$)alkyl).

In another embodiment the residue in compound (I) comprising the structural element is (C$_3$-C$_{15}$)heterocycloalkyl.

In another embodiment of the process of the present invention a residue containing the structural element in a compound (I) is selected from

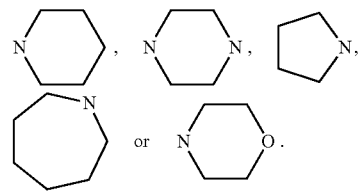

In another embodiment the present invention relates to a process for the preparation of a deuterated compound (II) containing at least one structural element of the formula N—C—C, which is not part of an aromatic ring system, and wherein the amount of deuterium at the carbon atom in the alpha position and/or the carbon atom in the beta position of the structural element is at least 1%, characterized in that a compound of formula (I) comprising a residue which contains at least one structural element N—C—C, wherein at least one H atom is at each carbon atom of the structural element and the N—C—C element is not part of an aromatic ring system, is reacted with a deuterium source in the presence of a catalyst of formula 1-UH-tetra-Z-cyclopentadienyl-(tetra-Z-2,4-cyclopentadien-1-U)-µ-hydro-tetra-L-diruthenium(II) (2) as defined herein, wherein the compound of formula (I) is $$R_1\text{-}L_1\text{-}V\text{-}L_2\text{-}W\text{-}L_3\text{-}X\text{-}L_4\text{-}Y \qquad (I)$$

wherein
R$_1$ is
H,
OH,
C(O)—(C$_1$-C$_6$)alkyl,
C(O)—V,
C(O)OR$_8$,
OC(O)—(C$_1$-C$_6$)alkyl,
OC(O)NR7R8,
OC(O)—V,
C(O)NR$_7$R$_8$,
Si—R$_7$,
OSiR$_7$,
NR$_7$—C(O)—(C$_1$-C$_6$)alkyl,
NR$_7$—C(O)O(C$_1$-C$_6$)alkyl,
NR$_7$—C(O)—V,
C(O)$_2$R$_8$,
NR$_7$—C(O)—NR$_7$R$_8$,
NR$_7$R$_8$,
SR$_8$,
S(O)—(C$_1$-C$_6$)alkyl,
S(O)—V,
S(O)$_2$NR$_7$R$_8$,
NR$_7$—SO$_2$—(C$_1$-C$_6$)alkyl,
NR$_7$—SO$_2$—(C$_1$-C$_6$)alkylene-V, NR$_7$—SO$_2$—V,
S(O)$_2$—(C$_1$-C$_6$)alkyl,
S(O)$_2$—OR$_8$, or
OS(O)$_2$—R$_8$;
R$_7$ is H, (C$_1$-C$_{12}$)alkyl, or phenyl;
R$_8$ is H, (C$_1$-C$_{12}$)alkyl;
L$_1$ is
a bond,
(C$_1$-C$_{12}$)alkylene, preferably (C$_1$-C$_6$)alkylene,
(C$_1$-C$_6$)alkenylene, or
(C$_2$-C$_6$)alkynylene;
L$_2$, L$_3$, or L$_4$ is independently of each other a group R$_2$—R$_3$—R$_4$ wherein
$_2$ and R$_4$ are independently of each other selected from
a bond,
O,
C(O),
C(O)CO,
C(O)NR$_7$,
NR$_7$C(O)
N(C(O)R7)
C(O)O,
OC(O),
NR$_7$,
S,
S(O),
S(O)$_2$,
S(O)$_2$—O,
OS(O)$_2$,
S(O)$_2$NR$_7$, or
NR$_7$S(O)$_2$;
R3 is
a bond,
(C$_1$-C$_{12}$)alkylene,
(C$_1$-C$_6$)alkenylene, or
(C$_2$-C$_6$)alkynylene;
with the proviso that R$_2$ or R$_4$ is a bond if R$_3$ is a bond;
V, W, X and Y are selected from
a bond,
(C$_3$-C$_8$)cycloalkyl,
(C$_5$-C$_{15}$)heteroaryl,
(C$_6$-C$_{10}$)aryl, or
(C$_3$-C$_{15}$)heterocycloalkyl,
wherein said (C$_6$-C$_{10}$)aryl, (C$_5$-C$_{14}$)heteroaryl, (C$_3$-C$_{15}$)heterocycloalkyl or (C$_3$-C$_8$)cycloalkyl is optionally substituted one, two, three or four times by a group independently of each other selected from R$_9$;
and wherein Y may also be H,
R$_9$ is
halogen,
oxo,
OH,
NO$_2$,
CN,
SO$_2$—N═CH—N[(C$_1$-C$_6$)alkyl]$_2$,
SF$_5$,
CF$_3$,
C(NH)(NH$_2$),
PO$_3$(R$_7$)$_{1-3}$,
R$_1$,
L$_1$-R1,
O-L$_1$-R$_1$,
V,
L1-V, or
O-L$_1$-V;
and a V substituent in R$_9$ may not be further substituted by a V substituent;

wherein in any alkyl or alkylene substituent one or more carbon atoms are optionally replaced by O, provided that two oxygens are not directly connected to each other, and wherein any alkyl or alkylene is optionally substituted by one, two or three residues independently of each other selected from
halogen, cyano, hydroxyl, O(C$_1$-C$_6$)Alkyl, S(C$_1$-C$_6$)alkyl, phenyl, O-phenyl, benzyl. OC(O)(C$_1$-C$_6$)alkyl, C(O)(C$_1$-C$_6$)alkyl, C(O)O(C$_1$-C$_6$)alkyl or C(O)OH.

The deuterated compound of formula (II) corresponds to the one of formula (I) with the difference of having deuterium incorporated in residues containing at least one of the defined structural element.

In one embodiment of a compound of formula (I) R$_1$ is NR$_7$R$_8$.

In one embodiment R$_7$ and R$_8$ are (C$_1$-C$_{12}$)alkyl, preferably (C$_1$-C$_6$)alkyl.

In a further embodiment L1 is a bond or (C$_1$-C$_{12}$)alkylene, preferably L1 is (C$_1$-C$_{12}$)alkylene, more preferably (C$_1$-C$_6$) alkylene.

In another embodiment R1-L1- is —NH(C$_1$-C$_{12}$)alkyl, —N((C$_1$-C$_{12}$)alkyl)$_2$, —(C$_1$-C$_{12}$)alkylene-N((C$_1$-C$_{12}$)alkyl)$_2$ or (C$_3$-C$_{15}$)heterocycloalkyl.

In a more specific embodiment, R1-L1- is —NH(C$_1$-C$_6$) alkyl. In another embodiment R1-L1- is N((C$_1$-C$_{12}$)alkyl)$_2$, preferably —N((C$_1$-C$_6$)alkyl)$_2$. In another embodiment R1-L1- is —(C$_1$-C$_{12}$)alkylene)-N((C$_1$-C$_{12}$)alkyl)$_2$, preferably —(C$_1$-C$_6$)alkylene)-N((C$_1$-C$_6$)alkyl)$_2$.

In another embodiment R1-L1 is (C$_1$-C$_{12}$)alkyl, preferably (C$_1$-C$_6$)alkyl.

In another embodiment the structural element may also be part of cyclic residues wherein the N-atom is part of that cyclic residue such as in a (C$_3$-C$_{15}$)hetero-cycloalkyl residue. Such a residue can be part of any of the V, W, X and Y residues.

In another embodiment of the process of the present invention one or more of the residues V, W, X or Y in a compound of formula (I) may comprise the structural element N—C—C.

In one embodiment one or more of V, W, X or Y is (C$_3$-C$_{15}$)heterocycloalkyl.

In a further embodiment thereof one or more of V, W, X or Y is, independently of each other, selected from

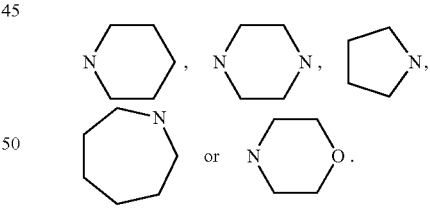

The substituents L$_1$, L$_2$, L$_3$ and L$_4$ may be attached at any carbon or N-atom.

More preferably one or more of V, W, X or Y is independently of each other selected from

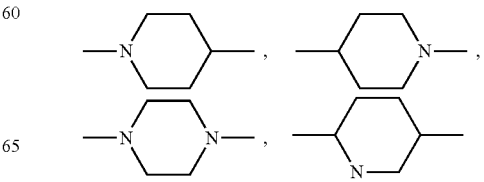

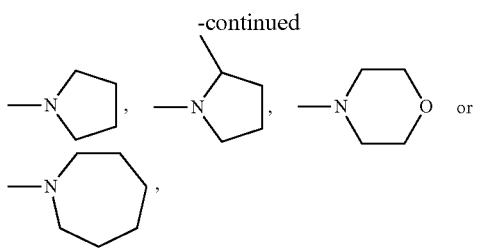

wherein $L_1$, $L_2$, $L_3$ or $L_4$ may be attached as indicated by the bonds (–), for example such as to give

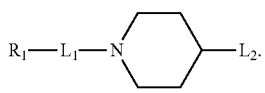

In another embodiment of a compound of formula (I) R2 is a bond, O, CO, C(O)O, NH, N(C(O)$R_7$), C(O)NH or NHC(O).

In another embodiment R3 is a bond, ($C_1$-$C_6$)alkenylene or ($C_1$-$C_6$)alkylene optionally substituted, independently of each other, one, two or three times by OH, halogen, C(O)O($C_1$-$C_6$)alkyl, OC(O)($C_1$-$C_6$)alkyl or optionally substituted phenyl.

In another embodiment $R_4$ is a bond, O, C(O), C(O)O, OC(O), S(O)$_2$, NH, NHC(O) or C(O)NH.

In another embodiment of the process L2, L3 or L4 is independently of each other a bond, CO, NH, ($C_1$-$C_6$)alkenylene or ($C_1$-$C_6$)alkylene optionally substituted one, two or three times by OH, halogen, C(O)O($C_1$-$C_6$)alkyl or is optionally substituted phenyl.

In one embodiment one or more of V, W, X and Y is ($C_6$-$C_{10}$)aryl, preferably phenyl.

In another embodiment $R_1$ is $NR_7R_8$, $L_1$ is ($C_1$-$C_6$)alkylene, V, W and X are a bond, $L_2$, $L_3$ and $L_4$ are a bond, Y is H.

In a further embodiment of a compound of formula (I) R1 is H, OH or $NR_7R_8$;
L1 is a bond or ($C_1$-$C_6$)alkylene;
V is a bond, ($C_6$-$C_{10}$)aryl preferably phenyl, ($C_3$-$C_8$)cycloalkyl, ($C_5$-$C_{15}$)heteroaryl or ($C_3$-$C_{15}$)heterocycloalkyl, preferably

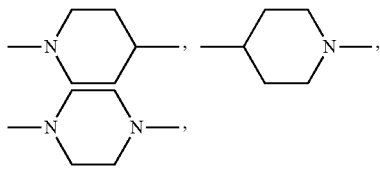

each of L2, L3 and L4 is R2-R3-R4, wherein
R2 is a bond, O, S(O)2, C(O), C(O)O, OC(O), NH, NHC(O), N(C(O)$R_7$) or C(O)NH;
R3 is a bond, (C1-C6)alkenylene or ($C_1$-$C_6$)alkylene optionally substituted one, two or three times by a group selected from ($C_1$-$C_6$)alkyl, C(O)—($C_1$-$C_6$)alkyl, OH, OC(O)—($C_1$-$C_6$)alkyl, or ($C_6$-$C_{10}$)aryl preferably phenyl, wherein ($C_6$-$C_{10}$)aryl is optionally substituted one, two three times by R9;
R4 is a bond, O, S(O)$_2$, NH, NHC(O), C(O)NH, C(O) or C(O)O, provided that R2 or R4 is a bond if R3 is a bond;
W and X is, independently of each other, a bond, ($C_6$-$C_{10}$)aryl preferably phenyl, ($C_3$-$C_8$)cycloalkyl, ($C_5$-$C_{15}$)heteroaryl or ($C_3$-$C_{15}$)heterocycloalkyl, and Y is H, ($C_6$-$C_{10}$)aryl preferably phenyl, ($C_3$-$C_8$)cycloalkyl, ($C_5$-$C_{15}$)heteroaryl or ($C_3$-$C_{15}$)heterocycloalkyl;
and any ($C_1$-$C_6$)alkylene in L1 and R3 is optionally substituted one, two or three times by a group selected from halogen, ($C_1$-$C_6$)alkyl, C(O)—($C_1$-$C_6$)alkyl, C(O)O($C_1$-$C_6$)alkyl, OH, OC(O)—($C_1$-$C_6$)alkyl, or phenyl, and/or one or more carbon atoms are optionally replaced by O;
and in L1, R3, V, W, X and Y any ($C_6$-$C_{10}$)aryl, ($C_5$-$C_{15}$)heteroaryl or ($C_3$-$C_{15}$)heterocycloalkyl is optionally substituted one, two, or three times by R9.

In another embodiment $R_1$ is $NR_7R_8$, $L_1$ and V are a bond, $L_2$ is R2-R3-R4, wherein R2 is a bond, R3 is ($C_1$-$C_6$)alkylene optionally substituted one, two or three times by a group independently of each other selected from ($C_1$-$C_6$)alkyl; C(O)—($C_1$-$C_6$)alkyl; OH, OC(O)—($C_1$-$C_6$)alkyl, and phenyl, wherein phenyl is optionally substituted one, two three times by R9; R4 is a bond, NHC(O) or C(O)NH;
W is ($C_3$-$C_8$)cycloalkyl, ($C_5$-$C_{15}$)heteroaryl, ($C_6$-$C_{10}$)aryl or ($C_3$-$C_{15}$)heterocycloalkyl optionally substituted by one, two, three or four times by a group independently selected from R9;
X is a bond or ($C_3$-$C_{15}$)heterocycloalkyl, L3 and L4 are a bond, and Y is H.

In a further embodiment of a compound of formula (I) R1 is H or OH; L1 is a bond or ($C_1$-$C_6$)alkylene;
V is phenyl or ($C_3$-$C_{15}$)heterocycloalkyl, preferably

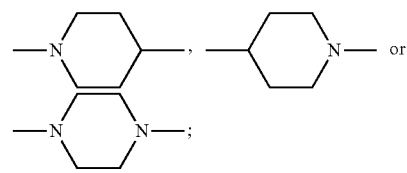

each of L2, L3 and L4 is R2-R3-R4, wherein
R2 is a bond, O, NHC(O) or C(O)NH,
R3 is a bond or ($C_1$-$C_6$)alkylene optionally substituted one, two or three times by a group selected from phenyl optionally substituted one, two three times by R9; ($C_1$-$C_6$)alkyl; C(O)—($C_1$-$C_6$)alkyl; OH or OC(O)—($C_1$-$C_6$)alkyl, and
R4 is a bond, O, S(O)2, NHC(O) or C(O)NH, provided that R2 or R4 is a bond if R3 is a bond;
W and X is, independently of each other, a bond, phenyl, ($C_5$-$C_{15}$)heteroaryl or ($C_3$-$C_{15}$)heterocycloalkyl, and
Y is H, a bond, phenyl, ($C_5$-$C_{15}$)heteroaryl or ($C_3$-$C_{15}$)heterocycloalkyl;
and wherein phenyl, ($C_5$-$C_{15}$)heteroaryl or ($C_3$-$C_{15}$)heterocycloalkyl is optionally substituted one, two three times by $R_9$.

In one embodiment $R_9$ is F, Cl, OH, $NH_2$, NH(($C_1$-$C_6$)alkyl), N(($C_1$-$C_6$)alkyl)$_2$, ($C_1$-$C_6$)alkyl, O($C_1$-$C_6$)alkyl, $CF_3$, CN, $SCH_3$, ($C_0$-$C_6$)alkyl-SO$_2$NHCH$_3$, or PO$_3$($R_7$)$_{1-3}$. In a further embodiment R9 is F, Cl, CN, OH, $NH_2$, $CF_3$, ($C_1$-$C_6$)alkyl or O($C_1$-$C_6$)alkyl.

Further embodiments of the present invention and conditions for introducing deuterium in the amine according to the process of present invention are outlined below.

In one embodiment according to the process of the present invention a catalyst of formula (2) is used as a catalyst wherein UH is OH and U is O. In another embodiment UH is $NHR_5$ and U is $NR_5$. In one embodiment $R_5$ is phenyl. In another embodiment each Z is optionally substituted phenyl, i.e. the catalyst contains tetra phenyl groups at the cyclopentadienyl. In a further embodiment said phenyl is not substituted. In another embodiment Z is unsubstituted phenyl, UH is OH, U is O and L is CO, to give 1-Hydroxy-tetraphenyl-cyclopentadienyktetraphenyl-2,4-cyclopentadien-1-one)-μ-hydrotetracarbonyldiruthenium(II) as catalyst.

The Shvo catalyst is commercially available. The catalyst and its derivatives may also be prepared by refluxing $Ru_3(CO)_{12}$ and tetraphenyl cyclopentadienone or corresponding substituted cyclopentadienons in a suitable solvent such as in methanol for a certain time such as 2 days (Casey et al. J. Am. Chem. Soc. 2001, 123, 109) or by methods described in the literature such as in e-EROS, Encycl. Reagents Org. Synth. 2009, 7, 5557-5564, Mays et al. Organometallics 1989, 8, 1162-1167, Conley et al. Chem. Rev. 2010, 110, 2294-2312 or in analogy to the methods described by L. Lewis in J. Am. Chem. Soc. 1986, 108, 743-749.

The amount of catalyst used in the process is not critical. In various embodiments of the process of the present invention, the amount of the catalyst used may vary and is typically in the range of 0.1 mol %-500 mol %, 1 mol %-100 mol %, 1 to 50 mol %, 5 mol %-50 mol % or 5-25 mol %, respectively, relative to a compound used as a reactive substrate. The amount of catalyst needed depends on the substrate and the intended reaction time and can be determined by a simple pre-test.

It is an advantage that the process is almost specific for the alpha and/or beta position. In a compound prepared according to the process of the present invention deuterated molecules contain at least one D-atom in the alpha position (carbon (C) atom bonded to the N-atom) and/or one D atom in the beta position. If both positions are deuterated, the compound (product) may contain molecules wherein the structural element is N-CD-CD, N-CD2-CD, N-CD-CD2, or N-CD2-CD2. If one position is deuterated, molecules containing N-CD-C, N—C-CD, N-CDD-C or N—C-CDD may be obtained. In compounds with an ethyl group as residue having no further bond but H at the second carbon could give additionally molecules with an N—C-CDDD, NCD-CDDD or N-CDD-CDDD deuteration pattern.

In the compound finally obtained all these molecules may exist as a mixture thereof. The amount of D-atoms introduced in the alpha relative to the beta position as well as the amount of deuterium introduced within the alpha and the beta position may vary depending on the structure of the overall molecule used as a substrate for reaction in the process of the present invention.

In order to obtain deuterium enriched compounds it is necessary to have a process where compounds can be obtained which contain more deuterium over what is already present due to the natural abundance (0.015%) of deuterium. In one embodiment of the process of the present invention a compound with at least 1% deuterium in the alpha and/or in beta position is obtained. This includes molecules having at least 1% deuterium in the alpha position or 1% in the beta position of the structural element as well as those having 1% percent in the alpha and 1% in the beta position of the structural element.

In a further embodiment of a compound prepared by the process of the present invention the amount of deuterium at one or both carbon atoms in the N—C—C element (in the alpha and/or beta position) is, independently of the alpha or beta position, at least 10%. In other embodiments, the amount of deuterium in the alpha and/or beta position is, independently of each position, at least 20%, 30%, 40%, 50%, 60%, 70%, 80%, or 90%, respectively. In an embodiment the amount of deuterium may be 100%. By way of example, a deuterated compound may contain at least 20% deuterium in the alpha position and/or at least 50% deuterium in the beta position of the structural element.

The percentage of deuterium is given relative to the total number of H atoms in the alpha and beta position, respectively.

In a particular embodiment of the process of the present invention a compound (II) is prepared wherein the alpha and the beta position in the structural element are deuterated.

A further embodiment of the present invention is a deuterated compound, such as a compound (II), prepared according to the process of the present invention.

The process according to the invention does not require multi-step syntheses with expensive deuterated starting materials, such as $D_2$ gas or deuterides like $NaBD_4$ or $LiAlD_4$, disproportional amounts of solvents or other cost intensive process steps, and thus can be used on larger scale. The process tolerates various functional groups and can be applied to complex organic molecule structures, e.g. pharmaceutically active compounds as well as to compounds for plant protection.

In a process of the present invention, examples of a deuterated solvent useful as a heavy hydrogen source, in the case where heavy hydrogen is deuterium, are deuterium oxide ($D_2O$), deuterated aliphatic alcohols such as deuterated methanol, deuterated ethanol (e.g. ethanol-$d_1$, -$d_5$, -$d_6$), deuterated propanol, deuterated isopropanol (e.g. isopropanol-$d_1$ and -$d_8$), deuterated butanol, deuterated tert-butanol, deuterated pentanol, deuterated hexanol, deuterated heptanol, deuterated octanol, deuterated nonanol, deuterated decanol, deuterated undecanol and deuterated dodecanol, deuterated cyclic alcohols such as deuterated cyclopentanol and deuterated cyclohexanol, deuterated dioles such as deuterated ethyleneglycol, deuterated propanediol, deuterated butanediol, deuterated pentanediol, deuterated ketones such as deuterated acetone, deuterated methyl ethyl ketone, deuterated methyl isobutyl ketone, deuterated diethyl ketone, deuterated dipropyl ketone, deuterated diisopropyl ketone and deuterated dibutyl ketone, deuterated cyclopentanone, deuterated cyclohexanone. In one embodiment deuterium oxide and deuterated alcohols are used. In another embodiment deuterium oxide, deuterated isopropanol and deuterated tert-butanol are used. In yet another embodiment deuterium oxide is used.

In another embodiment tritium may be incorporated as well. Specific examples of a tritium source include tritium oxide ($T_2O$), tritiated isopropanol etc. Accordingly, preparing tritium containing compounds of formula (II) according to the process of the present invention is also an object of the invention.

The deuterated solvent may be one wherein at least one hydrogen atom in a molecule is deuterated, such as, for example, a deuterated alcohol, wherein at least a hydrogen atom in a hydroxyl group is deuterated, or a ketone wherein at least the alpha-hydrogen atoms are replaced with deuterium, can be used in the process of the present invention. A solvent wherein all hydrogen atoms in the solvent molecule are deuterated is particularly preferred.

If the amount of a deuterated solvent used is increased, deuteration according to the present invention tends to proceed further. However, in view of cost, the amount of a deuterated solvent is used in an amount, as lower limit, of generally not less than equimolar, preferably in the order of, not less than 10 molar times, 20 molar times, 30 molar times and 40 molar times, and, although there is theoretically no limit, the upper limit is about 250 molar times, preferably 150 molar times, of a heavy hydrogen atom contained in the deuterated solvent, relative to hydrogen atoms which can be replaced by deuterium in the substrate.

In the process of the present invention it is preferred to carry out the hydrogen deuterium exchange (HDE) neat in the deuterium source. However, in case where a compound having an amine functionality as a reactive substrate in a method of the present invention precipitates in a deuterated solvent or is solid and hardly dissolves in a deuterated solvent, a co-solvent may be used in combination with the deuterated solvent, if necessary.

Examples of a co-solvent to be used include organic solvents which are not deuterated, and comprise ethers such as dimethyl ether, diethyl ether, diisopropyl ether, ethylmethylether, tert-butylmethyl ether, 1,2-dimethoxyethane, oxirane, 1,4-dioxane, dihydropyrane and tetrahydrofuran; aliphatic hydrocarbons such as hexane, heptane, octane, nonane, decane and cyclohexane; aromatic hydrocarbons such as benzene, toluene; halogenated solvents such as dichloromethane, 1,2-dichloroethane, chloroform and chlorobenzene; or other common solvents such as dimethoxyethane dimethylformamide, dimethylsulfoxide, or N-methylpyrrolidone.

Other organic co-solvents, which, if deuterated, can be used as deuterium source but which in non-deuterated form can also be used as co-solvent, are selected from water, alcohols such as methanol, ethanol, isopropanol, butanol, tert-butanol, pentanol, hexanol, heptanol, octanol, nonanol, decanol, undecanol and dodecanol; carboxylic acids such as formic acid, acetic acid, propionic acid, butyric acid, isobutyric acid, valeric acid, isovaleric acid and pivalic acid; ketones such as acetone, methylethylketone, methylisobutylketone, diethylketone, dipropylketone, diisopropylketone and dibutylketone. In case of protic solvents it is recommended to employ the deuterated form, e.g. $CH_3OD$ instead of $CH_3OH$.

The amount of co-solvent may vary depending on the substrate and is usually in the range of 10-90% (w/w) relative to the total amount of solvent used.

The reaction mixture comprising the deuterium source as solvent and a compound of formula (I) and optionally a co-solvent, which can be aqueous, aqueous-organic or pure organic, and thus, depending on miscibility, the reaction mixture may be homogeneous or heterogeneous.

For optimal performance of the reaction it is advised to avoid strongly acidic or basic conditions. It may be advantageous, to buffer the pH of the reaction mixture. A suitable pH range would be pH 3-12. It is recommended to use the compounds in its free base form for efficient deuteration. Thus salts (e.g. a hydrochloride salt) of a compound is preferably converted into the free base before deuteration.

The reaction can be performed in a sealed glass flask, a reaction vessel, a sealed pressure tube or a sealed microwave flask, most preferably in a sealed pressure tube or a sealed microwave flask. In a method of the present invention the reaction temperature used is in the range of 100-200° C., preferably in the range of 110-160° C., and particular preferred in the range of 120-150° C. The reaction temperature can be adjusted by classical means like an oil bath, by using a heating mantle or by employing a microwave. However the type of heating may influence the reaction times required to achieve similar deuterium incorporations for a given substrate. Reaction time in a method of the present invention can vary and is usually in the range of 30 minutes to 100 hours, preferably 1 to 50 hours, more preferably 1 to 30 hours and more preferably 3 to 30 hours. Usually classical heating requires much longer reaction times compared to microwave enhanced reactions.

In process control and determination of deuterium incorporations can be performed by standard LC-MS and NMR analytics.

In case a particular high degree of deuteration is intended it might be advantageous to remove the used mixture of solvent and deuteration reagent and to repeat the HDE reaction with a fresh mix of solvent and deuterium source. The degree of deuteration for a given nitrogen substrate may be also adjusted by variation of the reaction time, temperature and deuteration source.

After completion of the reaction the deuterated compound, especially a compound of formula (II), can be isolated by usual work up procedures such as extraction, crystallization, distillation or by applying chromatographic methods, e.g. chromatography on silica gel or preparative HPLC.

As an example for performing the process according to the present invention, an appropriate pressure or microwave tube is charged with the substrate and the Shvo-catalyst under argon atmosphere. The deuterated solvent is added, followed by sealing the reaction system and reacting with stirring in an oil bath for about 6 to 100 hours or in the microwave for 30 min to about 24 hours. After completion of the reaction (using e.g. LC-MS as process control) the reaction mixture is cooled to room temperature. The organic layer is separated and the water phase is extracted with an appropriate organic solvent. The solvent of the combined organic layers is then removed in vacuum and the crude product further purified if necessary. The product is subjected to structural analysis by NMR and mass spectrum measurements.

In the process according to the present invention, wherein in the structural element N—C—C the N is optionally substituted by one or two H, i.e. is a group of the formula $H_2N$—C—C or HN—C—C, the hydrogen or both hydrogens bonded to the N-atom in the amine may be protected independently of each other with a suitable N-protecting group before the deuteration is done (for suitable protecting groups see P. G. M. Wuts, T. W. Greene; Greene's Protective Groups in Organic Synthesis, 4$^{th}$ edition, Wiley-Interscience), e.g. N-methyl-, N-t-butyl-, N-diphenylmethyl-, N-triphenylmethyl-, N-allyl-, N-propargyl-, N-3-acetoxypropyl-, N-methoxymethyl-, N-benzyl-, N-4-methoxybenzyl-, N-2,4-dimethoxybenzyl-, N-methoxyphenyl-, N-9-phenylfluorenyl-, N-diphenylmethylene-, N-benzyliden-, N-1,1-dimethylthiomethylene-, 2,5-Dimethylpyrrol (J. Organic Cemistry 1998, 63, 4570), 1,2-bis(dimethylsilyl)benzene (Tetrahedron Letters 1990, 31, 6725).

In a further embodiment the following known pharmaceutical active compounds as described below by its formula and international non-proprietary name (INN), which contain the structural element N—C—C in various embodiments, may be prepared deuterium enriched in the alpha and/or beta position to the N-atom according to the process of the present invention.

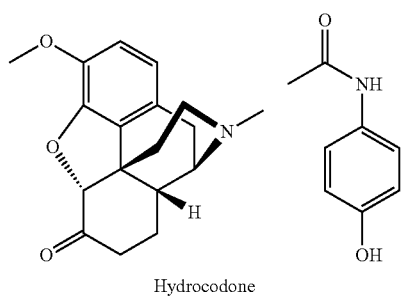

Hydrocodone

-continued
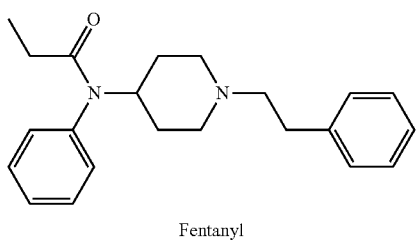
Fentanyl
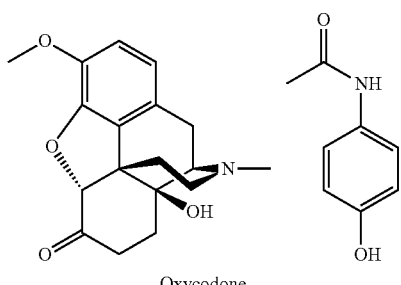
Oxycodone
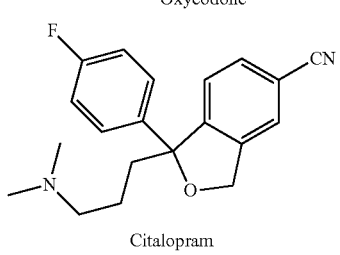
Citalopram
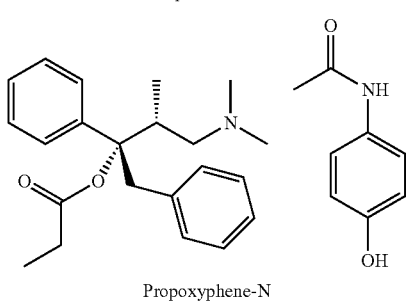
Propoxyphene-N
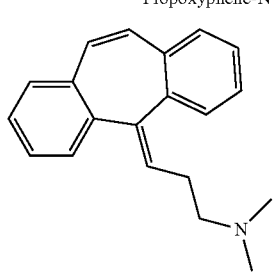
Cyclobenzaprine
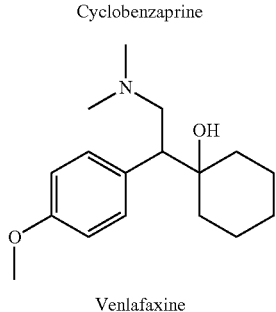
Venlafaxine
-continued
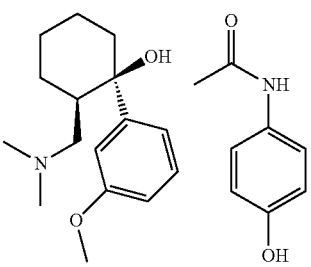
Tramadol
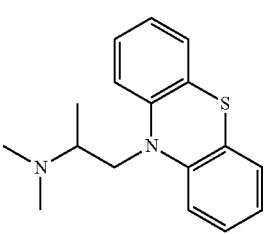
Promethazine
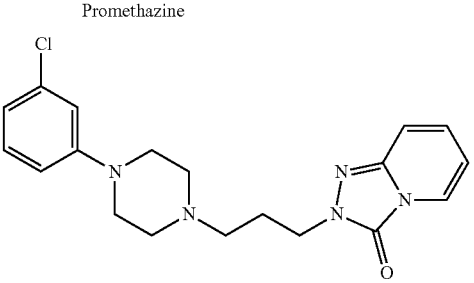
Trazodone
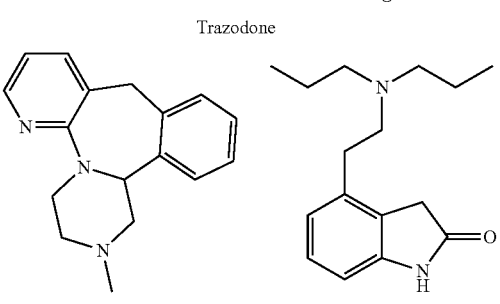
Mirtazapine    Ropinirole
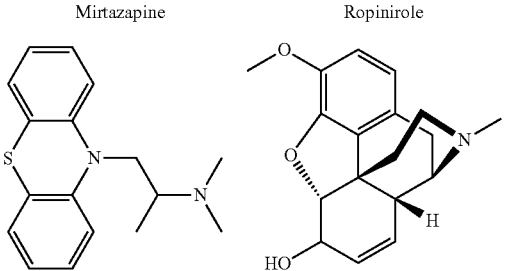
Promethazine/Codeine
Methadone

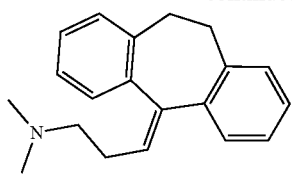
Amitriptyline
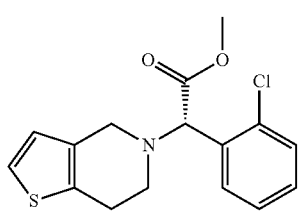
Clopidogrel
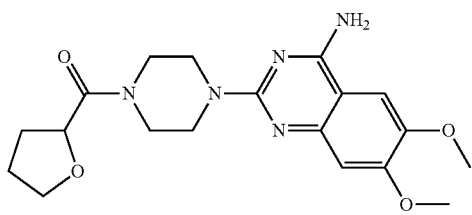
Terazosin
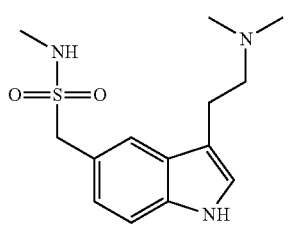
Sumatriptan
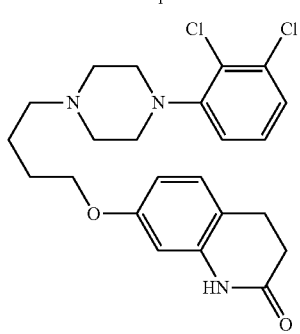
Aripiprazole
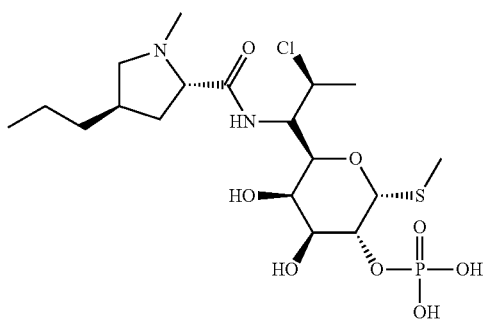
Clindesse
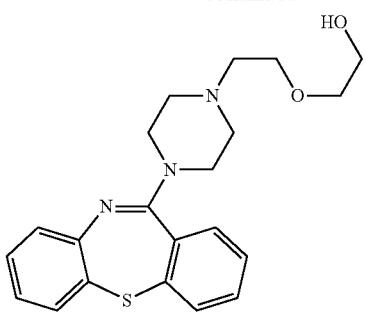
Quetiapine
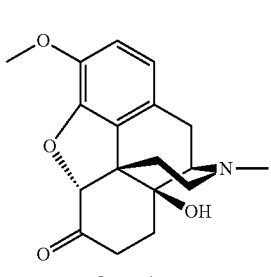
Oxycodone
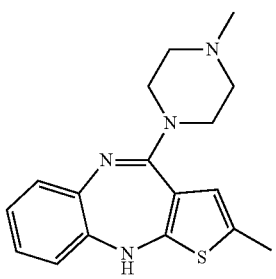
Olanzapine
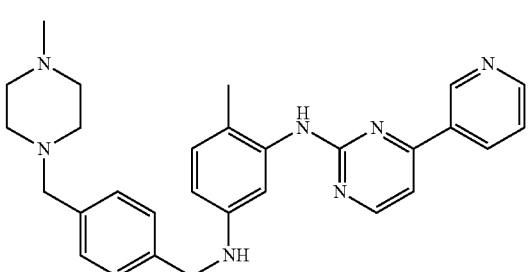
Imatinib
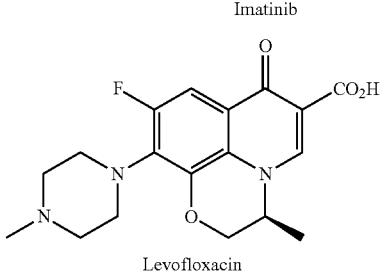
Levofloxacin

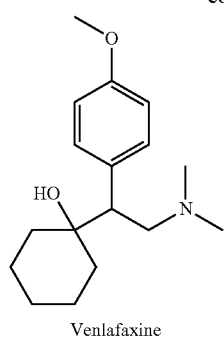
Venlafaxine
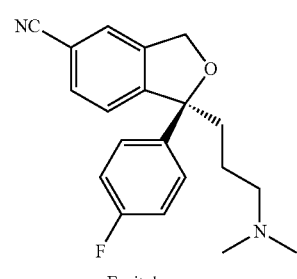
Escitalopram
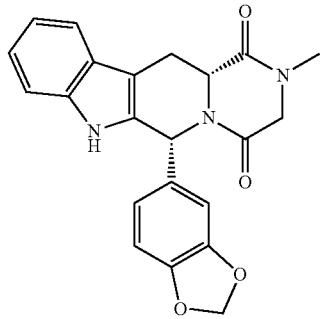
Tadalafil
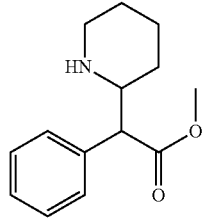
Methylphenidate
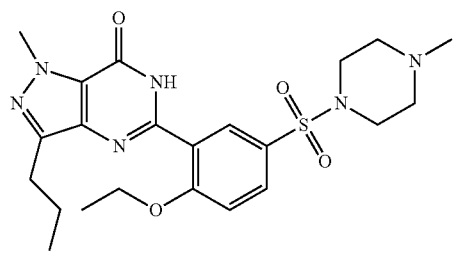
Sildenafil
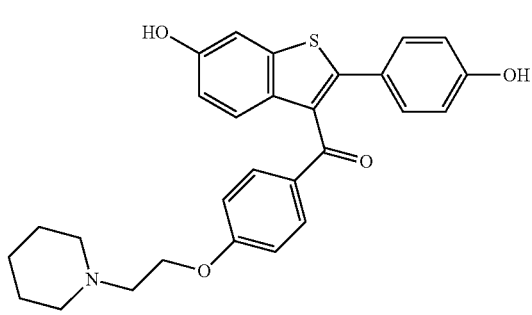
Raloxifene
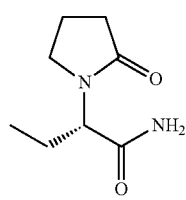
Levetiracetam
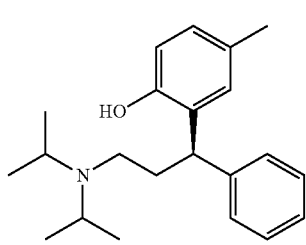
Tolderodine
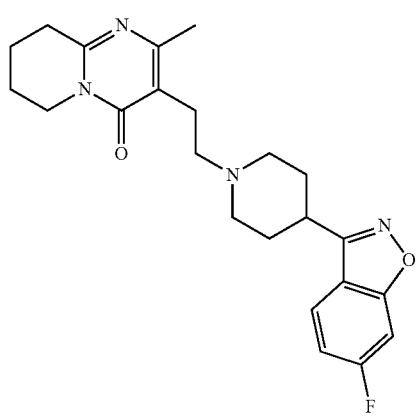
Risperidone
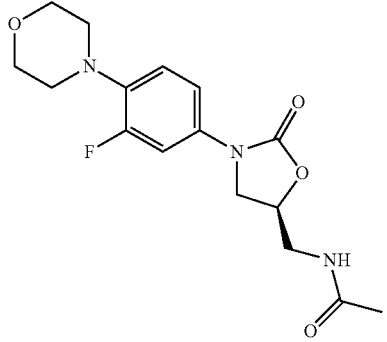
Linezolid
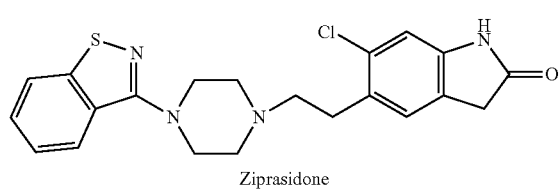
Ziprasidone -continued

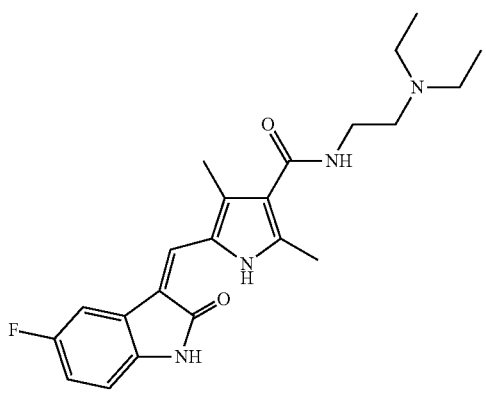

Sunitinib

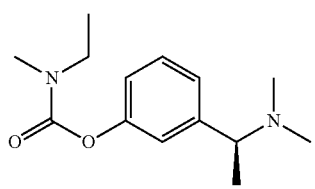

Rivastigmine

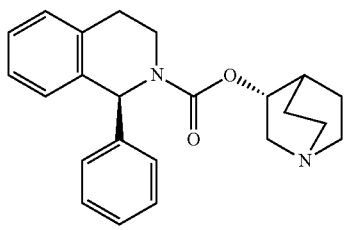

Solifenacin

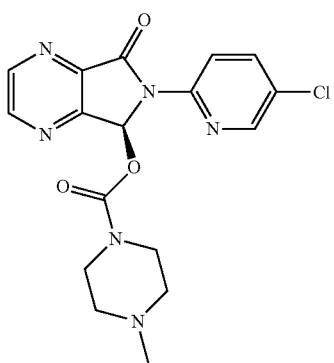

Eszopiclone

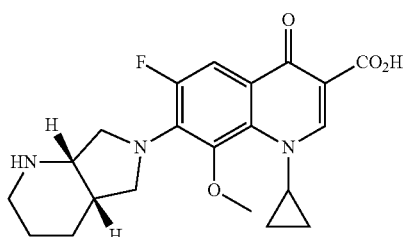

Moxiflocacin

-continued

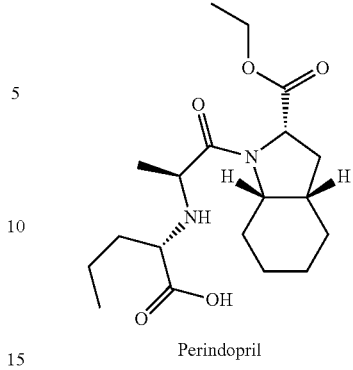

Perindopril

The deuteration of some of these compounds is also described in the Examples. For deuteration these compound can be prepared before by methods as described in the art.

In the following Examples, the present invention is explained in further detail without being limited thereto.

EXAMPLES

General Method A

Deuteration of Amines Under Thermal Conditions

Into a pressure tube was placed 0.025 mmol (5 mol %; relative to substrate) Shvo-catalyst (1-Hydroxy-tetraphenyl-cyclopentadienyktetraphenyl-2,4-cyclopentadien-1-one)-μ-hydrotetracarbonyldiruthenium(II)) and the flask was charged with argon. Then 0.5 mmol substrate, 0.1-2 mL toluene and 0.5-5 mL deuterium-source (e.g. $D_2O$) was added. The reaction vessel was sealed and heated for several hours (h) at 110 to 170° C. After cooling to room temperature the organic layer was separated. The aqueous phase was extracted three times by methyl-tertbutylether (MTBE) and the combined organic phases were dried over $MgSO_4$. The solvent was removed in vacuo and the crude product purified by chromatography on silica gel.

In some experiments the ratio of catalyst and substrate was varied. In some experiments toluene was substituted by another co-solvent or omitted.

General Method B

Deuteration of Amines Under Microwave Conditions

Into a microwave flask was placed 0.05 mmol (10 mol %, relative to substrate) Shvo-catalyst and the flask was charged with argon. Then 0.5 mmol substrate, respectively, 0.1-2 mL toluene and 0.5-5 mL Deuterium-source (e.g. $D_2O$) was added. The reaction vessel was sealed and heated in a microwave (e.g. OEM Corporation: Discover SP) for 1-2 hours at 110 to 170° C. (dynamic mode, $T_{max}$ 170° C., $P_{max}$ 300 W, $p_{max}$ 17 bar, stirring: high). After cooling to room temperature the organic layer was separated. The aqueous phase was extracted three times by methyl-tertbutylether (MTBE) and the combined organic phases were dried over $MgSO_4$. The solvent was removed in vacuo and the crude product purified by chromatography on silica gel.

In some experiments the ratio of catalyst and substrate was varied. In some experiments toluene was substituted by another co-solvent or omitted.

Determination of the Degree of Deuteration

In the following examples, the deuteration ratio of a hydrogen atom in each position of an isolated compound is shown. Deuteration ratio means ratio of amount of deuterated atoms to amount of deuteratable hydrogen atoms in a compound isolated after completion of the reaction. Deuteration ratio is given in [%] at the alpha and beta position in the structural element present in the formula.

The mean amount of deuterium per molecule of a mixture containing n isotopologues with the respective masses m, m+1, . . . , m+n was determined by mass spectrometry. Quantification was performed by subtracting the mean molecular mass of the undeuterated starting material from the mean molecular mass of the product mixture, whereas the resulting mass difference equals the mean amount of deuterium incorporated per molecule. The mean molecular masses were calculated as the sum of the relative signal intensities $A_i$ of a given isotopologue multiplied with the corresponding $m_i/z$ values derived from the mass spectrum.

Additionally or alternatively the deuteration can be determined by NMR methods. The assignment of signals (position of the deuterium) was determined by comparison of $^1$H NMR spectra of deuterated and non-deuterated compounds. In certain cases (overlapping signals or complicated spectra) $^{13}$C NMR and two-dimensional NMR spectra (COSY, NOESY, and proton-carbon correlation spectra, respectively) must be recorded to prove the assignment. The value of exchanged hydrogens was determined by integration of the remaining proton signals, using an internal standard such as anisic acid or dioxane. If signals of non-deuterated groups are present, these signals in the $^1$H NMR spectra can be used as standard. Quantification using an internal standard can be performed in the following way: First, $^1$H-NMR spectra of unlabelled starting materials were measured and $^1$H-NMR shifts for all signals determined. Subsequently, equimolar amounts of the deuterated product and an internal standard e.g. 5 µmol each were weighed into an NMR tube and dissolved in an appropriate deuterated organic solvent, e.g. DMSO-$d_6$, CDCl$_3$, CD$_2$Cl$_2$ etc. For calculation of percent deuterium incorporation in the resulting $^1$H-NMR-spectra peak areas of signals for deuterated positions were compared with those from the internal standard.

By way of example, N(CH$_2$—CH$_2$—CH$_2$—CH$_3$)$_3$ (see Ex. 1) contains 6H atoms in the alpha and 6 in the beta position of the N-atom. Thus the maximum of deuteration possible in each of these positions would be 6 D or, if both are taken together, 12 D. With a deuteration ratio of 92% obtained in the alpha position (corresponding to an average of 5.5 D) almost a complete exchange of H against D took place in all the positions next to the nitrogen (see Ex. 1). Taken together with 97% deuteration obtained in the beta position, about 89% of the molecules in the finally isolated compound were fully deuterated in the alpha and the beta position (100% deuteration).

In the Examples yield means yield of a compound isolated after completion of the reaction and work up irrespective of whether the compound is deuterated or not.

Materials

Shvo catalyst, which is also named ((1-Hydroxy-tetraphenylcyclopentadienyl-(tetraphenyl-2,4-cyclopentadien-1-one)-µ-hydrotetracarbonyldiruthenium(II)), was obtained commercially by Aldrich or can be prepared by known methods described in the literature.

Unless otherwise mentioned the compounds used in the examples were obtained from commercial sources such as Aldrich or Acros or can be prepared by methods known in the art.

Example 1

Tributylamine

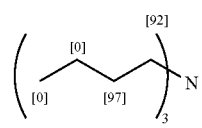

The reaction was performed according to general method A:

0.5 mmol (119 µL) tributylamine, 0.025 mmol (21.7 mg) Shvo, 1 mL D$_2$O, 1 mL toluene, 150° C., 24 h. Yield: 61%;

MS (EI, 70 eV) m/z (rel. int.): 197 (6), 196 (3), 185 (0) [M$_0$]$^+$, 153 (11), 152 (100), 151 (41), 108 (28), 107 (9), 64 (6), 48 (5).

$^1$H NMR (300 MHz, CDCl$_3$): δ=1.08 (t, J=6.9 Hz, 9H), 1.35-1.47 (m, 4H), 1.48-1.52 (m, 0.2H), 2.30-2.35 ppm (m, 0.3H).

Example 2

Trihexylamine

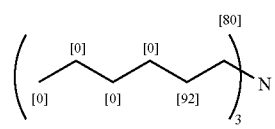

The reaction was performed according to general method A:

0.5 mmol (134 µL) trihexylamine, 0.025 mmol (21.7 mg) Shvo, 1 mL D$_2$O, 1 mL toluene, 150° C., 24 h. Yield: 70%;

MS (EI, 70 eV) m/z (rel. int.): 280 (3), 279 (3), 269 (0) [M$_0$]$^+$, 209 (7), 208 (57), 207 (100), 206 (67), 205 (21), 136 (6), 135 (11), 134 (9), 133 (5), 105 (5), 46 (6), 45 (6), 44 (6), 43 (5).

$^1$H NMR (300 MHz, CDCl$_3$): δ=1.07 (t, J=6.9 Hz, 9H), 1.39-1.54 (m, 18.2H), 2.48-2.55 ppm (m, 1.1H).

Example 3

Trioctylamine

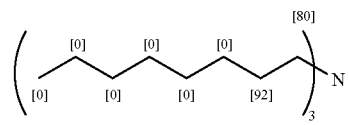

The reaction was performed according to general method A:

0.5 mmol (176 μL) trioctylamine, 0.025 mmol (21.7 mg) Shvo, 1 mL D$_2$O, 1 mL toluene, 150° C., 24 h. Yield: 65%;

MS (EI, 70 eV) m/z (rel. int.): 364 (3), 363 (3), 362 (2), 353 (0) [M$_{0]}$$^+$, 265 (10), 264 (63), 263 (100), 262 (4), 261 (27), 163 (5), 162 (5), 43 (6).

$^1$H NMR (300 MHz, CDCl$_3$): δ=1.03 (t, J=6.9 Hz, 9H), 1.34-1.51 (m, 30.5H), 2.42-2.54 ppm (m, 1.1H).

Example 4

Triisopentylamine

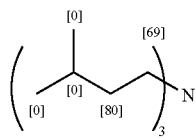

The reaction was performed according to general method A:

0.5 mmol (145 μL) triisopentylamine, 0.025 mmol (21.7 mg) Shvo, 1 mL D$_2$O, 1 mL toluene, 150° C., 24 h. Yield: 75%;

MS (EI, 70 eV) m/z (rel. int.): 238 (3), 237 (7), 236 (9), 235 (6), 227 (0) [M$_{0]}$$^+$, 234 (3), 180 (12), 179 (51), 178 (100), 177 (99), 176 (48), 175 (19), 122 (8), 121 (25), 120 (38), 119 (33), 118 (16), 117 (7), 64 (9), 63 (21), 62 (24), 61 (16), 60 (7), 47 (7), 46 (11), 45 (13), 44 (9), 43 (13), 42 (5), 41 (7).

$^1$H NMR (300 MHz, CDCl$_3$): δ=0.86 (d, J=6.6 Hz, 18H), 1.21-1.34 (m, 1.52H), 1.51 (p, 3H), 2.25-2.44 ppm (m, 2.1H).

Example 5

Tris-[2-(2-methoxy-ethoxy)-ethyl]-amine

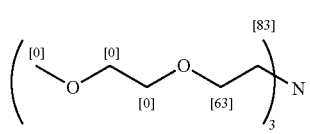

The reaction was performed according to general method A:

0.5 mmol (160 μL) tris-[2-(2-methoxy-ethoxy)-ethyl]-amine, 0.025 mmol (21.7 mg) Shvo, 1 mL D$_2$O, 1 mL toluene, 150° C., 24 h. Yield: 58%;

MS (EI, 70 eV) m/z (rel. int.): 323 (0) [M$_{0]}$$^+$, 244 (33), 243 (61), 242 (100), 241 (88), 240 (64), 239 (29), 238 (8), 108 (6), 107 (9), 106 (12), 105 (8), 63 (5), 62 (7), 61 (8), 60 (10), 59 (70), 58 (6), 46 (7), 45 (18), 31 (10), 29 (11).

MS (ESI) m/z (%): 324 (0) [M$_0$+H]$^+$, 328 (2), 329 (10), 330 (14), 331 (20), 332 (19), 333 (16), 334 (14), 335 (5), 336 (1).

$^1$H NMR (300 MHz, CDCl$_3$): δ=2.74 (t, J=6.3 Hz, 1H), 3.29-3.38 (m, 9H), 3.42-3.64 ppm (m, 15.8H).

Example 6

Butyldiethylamine

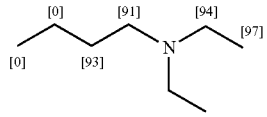

The reaction was performed according to general method A:

0.5 mmol (86 μL) diethylbutylamine, 0.025 mmol (21.7 mg) Shvo, 1 mL D$_2$O, 1 mL toluene, 150° C., 24 h. Yield: 57%;

MS (EI, 70 eV) m/z (rel. int.): 143 (7), 142 (6), 129 (0) [M$_{0]}$$^+$, 125 (5), 99 (6), 98 (100), 97 (73), 96 (16), 81 (13), 80 (8), 66 (9), 65 (8), 46 (8), 34 (9), 30, (7).

$^1$H NMR (300 MHz, i-PrOH-d$_8$): δ=1.05 (t, J=7.4 Hz, 3H), 1.08-1.16 (m, 0.2H), 1.42 (tq, J=7.1 Hz, J=7.2 Hz, 2H), 1.47-1.60 (m, 0.2H), 2.50 (s, 0.2H), 2.59 ppm (s, 0.3H).

Example 7

(1-Ethyl-propyl)-diisopropyl-amine

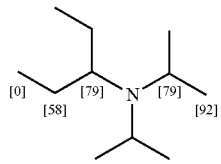

The reaction was performed according to general method A:

0.5 mmol (108 μL) (1-ethyl-propyl)-diisopropyl-amine, 0.025 mmol (21.7 mg) Shvo, 3 mL i-PrOH-d$_8$, 150° C., 24 h. Yield: 47%;

MS (EI, 70 eV) m/z (rel. int.): 189 (4), 188 (8), 187 (6), 171 (5) [M$_0$]$^+$, 170 (9), 169 (5), 159 (14), 158 (61), 157 (100), 156 (48), 155 (7), 111 (6), 110 (17), 109 (14), 97 (6), (96 (6), 90 (6), 63 (13), 62 (20), 61 (8), 49 (10), 46 (9), 45 (7).

$^1$H NMR (300 MHz, CDCl$_3$): δ=0.85 (t, J=6.6 Hz, 6H), 0.90-0.99 (m, 1.4H), 1.20-1.47 (m, 2H), 2.21-2.38 ppm (m, 0.4H).

Example 8

Butylcycloheptylamine

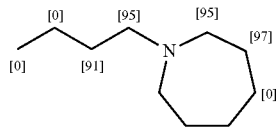

The reaction was performed according to general method A:

0.5 mmol (145 μL) butylcycloheptylamine, 0.025 mmol (21.7 mg) Shvo, 1 mL $D_2O$, 1 mL toluene, 150° C., 24 h. Yield: 49%;

MS (EI, 70 eV) m/z (rel. int.): 167 (7), 166 (8), 165 (3), 155 (0) $[M_0]^+$, 123 (7), 122 (100), 121 (95), 120 (32), 64 (12), 63 (11), 46 (9), 45 (7), 44 (6).

$^1$H NMR (300 MHz, i-PrOH-$d_8$): δ=1.04 (t, J=7.3 Hz, 3H), 1.42 (q, J=7.1 Hz, 2H), 1.47-1.62 (m, 0.2H), 1.70 (s, 4H), 1.72-1.80 (m, 0.1H), 2.48-2.56 (m, 0.1H), 2.64-2.73 ppm (s, 0.2H).

Example 9

N,N-Dimethyl-(2-phenylethyl)amine

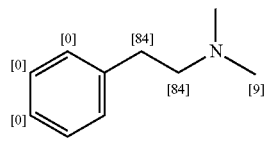

The reaction was performed according to general method A:

0.5 mmol (84 μL) N,N-dimethyl-(2-phenylethyl)amine 0.025 mmol (21.7 mg) Shvo, 1 mL toluene, 3 mL i-PrOH-$d_8$, 150° C., 24 h. Yield: 29%;

$^1$H NMR (300 MHz, CDCl$_3$): δ=2.30 (s, 5.4H), 2.45-2.57 (m, 0.4H), 2.71-2.80 (m, 0.2H) 7.15-7.24 (m, 3H), 7.24-7.34 ppm (m, 2H).

Example 10

N,N-Dibenzylethylamine

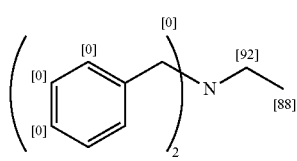

The reaction was performed according to general method A:

0.5 mmol (145 μL) N,N-dibenzylethylamine, 0.025 mmol (21.7 mg) Shvo, 1 mL $D_2O$, 1 mL toluene, 150° C., 24 h. Yield: 69%;

MS (EI, 70 eV) m/z (rel. int.): 231 (4), 230 (10), 229 (5), 225 (0) $[M_0]^+$, 214 (5), 213 (23), 212 (54), 211 (10), 181 (6), 153 (7), 93 (6), 92 (24), 91 (100), 65 (11).

$^1$H NMR (300 MHz, CDCl$_3$): δ=1.01 (br s, 0.4H), 2.45 (s, 0.2H), 3.56 (s, 4H), 7.21 (m, 2H), 7.30 (m, 4H), 7.37 ppm (m, 4H).

Example 11

1-Phenyl-pyrrolidine

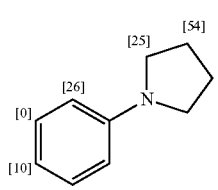 [SMILES: c1ccc(N2CCCC2)cc1]

The reaction was performed according to general method A:

0.5 mmol (119 μL) 1-phenyl-pyrrolidine, 0.025 mmol (21.7 mg) Shvo, 1 mL $D_2O$, 1 mL toluene, 150° C., 24 h. Yield: 80%;

MS (EI, 70 eV) m/z (rel. int.): 154 (3), 153 (20), 152 (63), 151 (100), 150 (99), 149 (65), 148 (19), 147 (4) $[M_0]^+$, 123 (7), 122 (9), 121 (6), 120 (5), 107 (6), 106 (11), 105 (14), 94 (25), 93 (51), 92 (23), 79 (7), 78 (21), 77 (22), 52 (6), 51 (10).

$^1$H NMR (300 MHz, CDCl$_3$): δ=1.82-1.96 (m, 3H), 3.12-3.23 (m, 1.8H), 6.48 (m, 1.5H), 6.48 (m, 0.9H) 7.09-7.18 ppm (m, 2H).

Example 12

1-Phenyl-piperidine

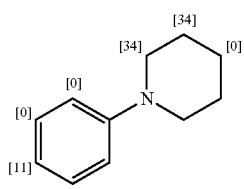 [SMILES: c1ccc(N2CCCCC2)cc1]

The reaction was performed according to general method A:

0.5 mmol (125 μL) 1-phenyl-piperidine, 0.025 mmol (21.7 mg) Shvo, 1 mL $D_2O$, 1 mL toluene, 150° C., 24 h. Yield: 73%;

$^1$H NMR (300 MHz, CDCl$_3$): δ=1.42-1.54 (m, 2H), 1.55-1.67 (m, 2.6H), 2.94-3.16 (m, 2.6H), 6.73 (m, 0.9H), 6.85 (m, 2H), 7.09-7.18 ppm (m, 2H).

Example 13

N,N-Dibutylphenylamine

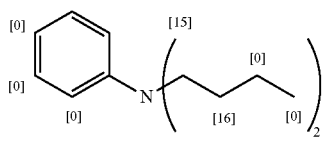

The reaction was performed according to general method A:

1 mmol (125 μL) N,N-dibutylphenylamine, 0.01 mmol (10.9 mg) Shvo, 2 mL D$_2$O, 1 mL toluene, 150° C., 24 h. Yield: 62%;

MS (EI, 70 eV) m/z (rel. int.): 208 (4), 207 (10), 206 (18), 205 (26) [M$_0$]$^+$, 165 (8), 164 (24), 163 (45), 162 (100), 122 (7), 121 (36), 120 (67), 107 (18), 106 (59), 105 (7), 104 (12), 91 (6), 79 (6), 78 (5), 77 (26), 57 (5), 50 (5), 41 (10), 29 (8).

$^1$H NMR (300 MHz, CDCl$_3$): δ=0.87 (t, J=7.4 Hz, 6H), 1.16-1.35 (m, 4H), 1.38-1.56 (m, 3.4H), 3.17 (t, J=7.6 Hz, 3.5H), 6.45-6.62 (m, 3H), 7.06-7.15 ppm (m, 2H).

Example 14

1,1-Diphenyl-3-piperidin-1-yl-propan-1-ol

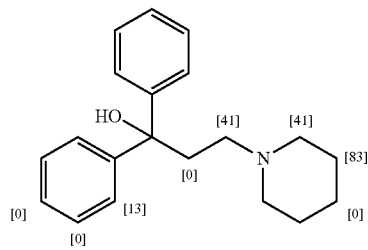 [SMILES: OC(CCN1CCCCC1)(c1ccccc1)c1ccccc1]

The reaction was performed according to general method A:

0.5 mmol (125 μL) 1,1-diphenyl-3-piperidin-1-yl-propan-1-ol, 0.025 mmol (21.7 mg) Shvo, 3 mL i-PrOH-d$_8$, 150° C., 24 h. Yield: 67%;

MS (EI, 70 eV) m/z (rel. int.): 304 (2), 303 (3), 302 (2), 295 (0) [M$^+$], 181 (7), 180 (9), 179 (8), 178 (6), 121 (6), 120 (8), 119 (6), 107 (30), 106 (89), 105 (100), 104 (40), 103 (11), 93 (7), 92 (11), 91 (10), 90 (6), 78 (7), 77 (16), 60 (5), 45 (5), 44 (5). $^1$H NMR (300 MHz, CD$_3$OD): δ=1.51 (br s, 2H), 1.63-1.78 (m, 0.8H), 2.62-2.72 (m, 1.9H), 2.86-2.95 (m, 1.6H), 3.21 (m, 1.8H), 7.13 (m, 2H), 7.22 (m, 4H), 7.33 ppm (m, 3.6H).

Example 15

2-Diethylamino-1-phenyl-propan-1-ol

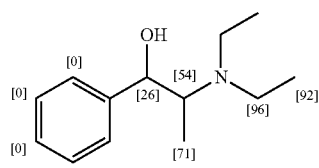

The reaction was performed according to general method A:

0.5 mmol (125 μL) 2-diethylamino-1-phenyl-propan-1-ol, 0.025 mmol (21.7 mg) Shvo; 3 mL i-PrOH-d$_8$, 1 mL toluene, 150° C., 24 h. Yield: 57%;

$^1$H NMR (300 MHz, CDCl$_3$): δ=0.74-0.82 (m, 0.9H), 1.13 (s, 0.5H), 2.40 (s, 0.2H), 2.67-2.79 (m, 0.2H), 4.20-4.27 (m, 0.6H), 4.85-6.00 (br s, 0.9H), 7.28-7.45 ppm (m, 5H).

Example 16

2-(4-{1-Hydroxy-4-[4-(3-hydroxy-3,3-diphenyl-propyl)-piperidin-1-yl]-butyl}-phenyl)-2-methyl-propionic acid, Fexofenadine (INN)

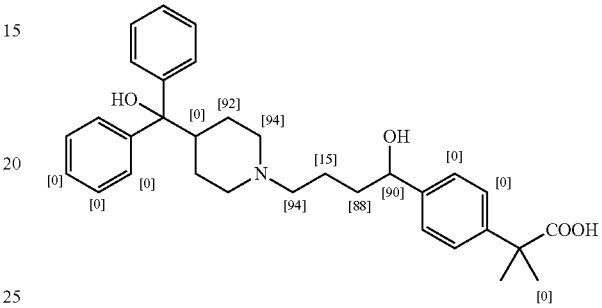

The reaction was performed according to general method A:

0.3 mmol (151 mg) fexofenadine (e.g. U.S. Pat. No. 4,254,129), 0.015 mmol (16.3 mg)

Shvo, 3 mL i-PrOH-d$_8$, 1 mL toluene, 150° C., 24 h. Yield: 48%;

$^1$H NMR (500 MHz, CD$_3$OD): δ=1.28-1.68 (m, 8.5H), 1.83-1.89 (m, 0.2H), 2.00-2.05 (m, 0.1H), 2.34-2.39 (m, 1H), 2.92-2.96 (m, 0.1H), 4.56 (br s, 0.1H), 7.12 (m, 2H), 7.22 (m, 2H), 7.25 (m, 4H), 7.37 (m, 2H), 7.48 ppm (m, 4H).

Example 17

2-Diethylamino-N-(2,6-dimethyl-phenyl)-acetamide; Lidocaine (INN)

The reaction was performed according to general method B:

0.25 mmol (58.6 mg) lidocaine, 0.025 mmol (27.1 mg) Shvo, 25 mmol (1911 μL) i-PrOH-d$_8$, 500 μL toluene, 170° C., 2 h. Yield: 84%;

MS (EI) m/z (%): 242 (1), 241 (2), 240 (2), 239 (1), 234 (0) [M$_0$]$^+$, 121 (3), 120 (4), 119 (2), 118 (2), 95 (8), 94 (34), 93 (83), 92 (100), 91 (61), 90 (15), 89 (3), 79 (3), 78 (3), 77 (8), 76 (2), 65 (2), 64 (2), 63 (5), 62 (6), 61 (4), 60 (3), 59 (2), 46 (2), 45 (3), 44 (2), 33 (4), 32 (7), 31 (4), 30 (2).

$^1$H NMR (300 MHz, CDCl$_3$): δ=1.12 (br m, 3.3H), 2.23 (s, 6H), 2.69 (br s, 1.1H), 3.24 (br s, 0.7H), 7.00-7.15 (br m, 3H), 8.97 ppm (br s, 1H).

Example 18

4-Amino-5-chloro-N-(2-diethylamino-ethyl)-2-methoxy-benzamide, Metoclopramide (INN)

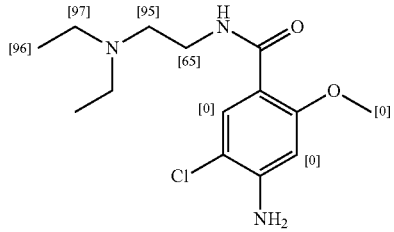 [SMILES: CCN(CC)CCNC(=O)c1cc(Cl)c(N)cc1OC]

The reaction was performed according to general method B:

0.25 mmol (75.0 mg) metoclopramide, 0.025 mmol (13.6 mg) Shvo, 400 mmol (1800 μL) D$_2$O, 150° C., 4 h. Yield: 23%;

LC-MS (ESI) m/z (%): 300 (0) [$^{35}$Cl-M$_0$+H]$^+$, 302 (0) [$^{37}$Cl-M$_0$+H]$^+$, 310 (1), 311 (5), 312 (20), 313 (31), 314 (23), 315 (13), 316 (6), 317 (1).

$^1$H NMR (300 MHz, CDCl$_3$): δ=1.18 (br m, 0.1H), 2.82 (br s, 0.1H), 2.90 (br s, 0.1H), 3.66-3.74 (m, 0.6H), 3.92 (s, 3H), 4.44 (s, 2H), 6.30 (s, 1H), 8.05 (s, 1H), 8.37 ppm (br s, 1H).

Example 19

(R)-(2,3-Dimethoxy-phenyl)-{1-[2-(4-fluoro-phenyl)-ethyl]-piperidin-4-yl}-methanol

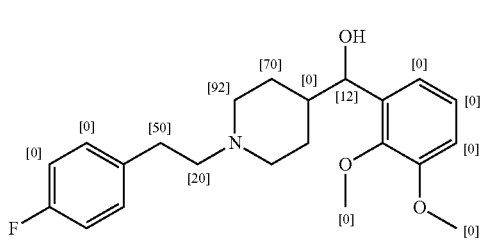 [SMILES: COc1cccc(C(O)C2CCN(CCc3ccc(F)cc3)CC2)c1OC]

The reaction was performed according to general method B:

0.1 mmol (38 mg) substrate (see e.g. U.S. Pat. No. 5,134, 149), 0.01 mmol (10.9 mg) Shvo, 40 mmol (3057 μL) i-PrOH-d$_8$, 200 μL toluene, 150° C., 4 h. Yield: 71%;

LC-MS (ESI) m/z (%): 374 (0) [M$_0$+H]$^+$, 384 (2), 385 (10), 386 (27), 387 (41), 388 (15), 389 (3), 390 (1).

$^1$H NMR (500 MHz, CDCl$_3$): δ=1.21-1.55 (m, 1H), 1.68 (m, 1H), 2.04 (m, 0.2H), 2.50-2.67 (m, 1.6H), 2.80 (m, 1H), 2.95-3.10 (m, 0.2H), 3.86, 3.86 (2 s, 6H), 4.65 (d, J=8.2 Hz, 0.8H), 6.84 (dd, J=8.0 Hz, J=1.4 Hz, 1H), 6.90 (dd, J=7.8 Hz, J=1.4 Hz, 1H), 6.94 (m, 2H), 7.04 ('t', J=8.0 Hz, J=7.8 Hz, 1H), 7.13 ppm (m, 2H).

Example 20

3-(4-fluorophenyl)-1-methylpiperazine

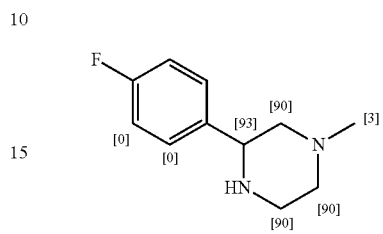

The reaction was performed according to general method B:

0.15 mmol (29.1 mg) substrate 0.015 mmol (16.3 mg) Shvo, 5 mmol (2348 μL) t-BuOD, 1 mL toluene, 150° C., 2 h. Yield: 74%;

MS (EI) m/z (%): 202 (1), 201 (4), 200 (2), 194 (0) [M$_0$]$^+$, 155 (6), 154 (3), 140 (2), 139 (6), 138 (4), 137 (2), 125 (12), 124 (11), 123 (12), 122 (28), 111 (7), 97 (6), 63 (19), 62 (100), 61 (26), 46 (9), 45 (14), 44 (6), 43 (9).

$^1$H NMR (500 MHz, CD$_3$OD): δ=2.00 (br, 0.1H), 2.13-2.22 (m, 0.2H), 2.28-2.34 (m, 2.9H), 2.79-2.95 (m, 0.3H), 3.00-3.11 (m, 0.2H), 3.79 (br s, 0.1H), 7.06 (m, 2H), 7.39 ppm (m, 2H).

Example 21

N-[2-(Diethylamino)ethyl]-5-[(Z)-(5-fluor-1,2-dihydro-2-oxo-3H-indol-3-yliden)-methyl]-2,4-dimethyl-1H-pyrrol-3-carboxamid; Sunitinib (INN)

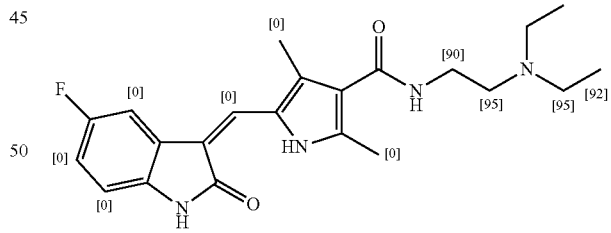

The reaction was performed according to general method B:

0.1 mmol (39.8 mg) substrate, 0.01 mmol (10.8 mg) Shvo, 40 mmol (3005 μL) t-BuOD, 150° C., 4 h. Yield: 67%;

LC-MS (ESI) m/z (%): 399 (0) [M$_0$+H]$^+$, 409 (2), 410 (5), 411 (14), 412 (28), 413 (30), 414 (17), 415 (4), 416 (1).

$^1$H NMR (500 MHz, DMSO-d$_6$): δ=0.77-0.95 (m, 0.7H), 2.42, 2.44 (2s, 6H), 2.44-2.47 (m, 0.2H), 3.25 (d, J=5.5 Hz, 0.1H), 6.84 (dd, J=8.7 Hz, J=4.6 Hz, 1H), 6.91 (ddd, J=9.5 Hz, J=8.5 Hz, J=2.5 Hz, 1H), 7.40 (s, 1H), 7.70 (s, 1H), 7.74 (dd, J=9.2 Hz, J=2.5 Hz, 1H), 10.89 (s, 1H), 13.68 ppm (s, 1H).

Example 22

4-Ethoxy-N-{4-[4-(6-trifluoromethyl-benzo[b]thiophen-3-yl)-piperazin-1-yl]-butyl}-benzamide

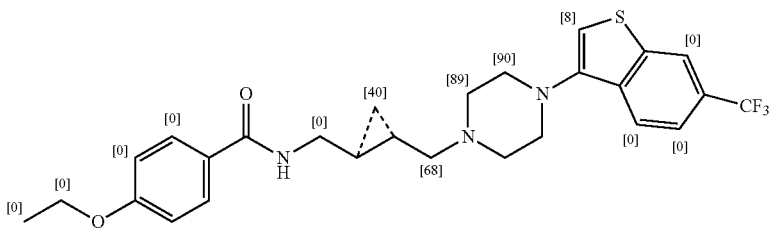 [SMILES: CCOc1ccc(C(=O)NC[C@H]2C[C@@H]2CN2CCN(c3csc4cc(C(F)(F)F)ccc34)CC2)cc1]

The reaction was performed according to general method B:

0.15 mmol (75.8 mg) substrate (obtainable in analogy as described in WO 02/066469 A2, Ex. 27), 0.015 mmol (16.7 mg) Shvo, 30 mmol (2817 µL) tBuOD, 1 mL toluene, 150° C., 2 h. Yield: 66%;

LC-MS (ESI) m/z (%): 506 (0) $[M_0+H]^+$, 514, (1), 515 (2), 516 (6), 517 (18), 518 (34), 519 (26), 520 (9), 521 (3), 522 (2).

$^1$H NMR (300 MHz, CDCl$_3$): δ=1.41 (t, J=7.0 Hz, 3H), 1.68 (t, J=6.9 Hz, 2.4H), 2.49 (br m, 0.6H), 2.67 (br m, 0.8H), 3.10 (br s, 0.5H), 3.47 (m, 2H), 4.05 (q, J=7.0 Hz, 2H), 6.55 (br t, 1H), 6.75 (s, 0.9H), 6.89 (m, 2H), 7.56 (dd, J=8.6 Hz, J=1.3 Hz, 1H), 7.73 (m, 2H), 7.80 (d, J=8.4 Hz, 1H), 8.07 ppm (br m, 1H).

Example 23

((S)-1-Methyl-pyrrolidin-2-yl)-diphenyl-methanol

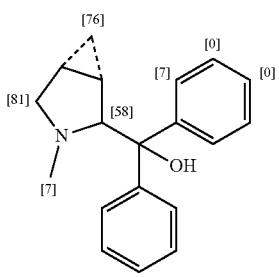 [SMILES: CN1C[C@@H]2C[C@@H]2C1C(O)(c1ccccc1)c1ccccc1]

The reaction was performed according to general method B:

0.075 mmol (20.1 mg) substrate, 0.0075 mmol (8.7 mg) Shvo, 30 mmol (541 µL) D$_2$O, 2 mL toluene, 150° C., 1 h. Yield: 52%;

LC-MS (ESI) m/z (%): 268 (0) $[M_0+H]^+$, 269 (4), 270 (13), 271 (22), 272 (22), 273 (16), 274 (14), 275 (7), 276 (1).

$^1$H NMR (300 MHz, CDCl$_3$): δ=1.47-1.67 (m, 0.7H), 1.74 (s, 2.7H), 1.76-1.89 (m, 0.3H), 2.24-2.38 (m, 0.2H), 2.93-3.06 (m, 0.2H), 3.49-3.62 (m, 0.4H), 3.81-5.29 (br s, 0.9H), 7.00-7.10 (m, 2H), 7.14-7.23 (m, 4H), 7.41-7.50 (m, 2H), 7.52-7.61 ppm (2H).

Example 24

1-[5-(4-tert-Butyl-piperazin-1-yl)-pyridin-2-yl]-1,2,3,4-tetrahydro-quinoxaline

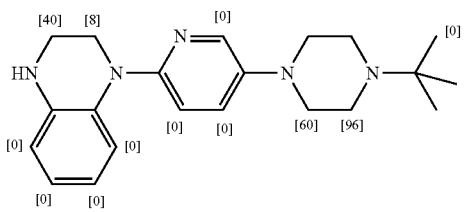

The reaction was performed according to general method B:

0.57 mmol (200 mg) substrate, 0.017 mmol (20 mg) Shvo, 55 mmol (1 mL) D$_2$O, 13 mmol (1 mL) i-PrOH-d$_8$, 150° C., 1.5 h. Yield: 76%;

LC-MS (ESI) m/z (%): 351 (0) $[M_0+H]^+$, 355, (1), 356 (3), 357 (22), 358 (60), 359 (100), 360 (100), 361 (73), 362 (32), 363 (15), 364 (6), 365 (1).

$^1$H NMR (500 MHz, ACN-d$_3$): δ=1.10 (s, 9H), 2.70 (br m, 1.6H), 3.05 (br s, 0.2H), 3.28 (m, 1.2H), 3.83 (m, 1.8H), 4.60 (br s, 1H, NH), 6.51 (t, J=7.1 Hz, 1H), 6.61 (dd, J=7.9 Hz, J=1.4 Hz, 1H), 6.75 (t, J=7.0 Hz, 1H), 6.99 (m, 2H), 7.20 (dd, J=9.0 Hz, J=3.0 Hz, 1H), 7.92 ppm (d, J=3.0 Hz, 1H).

Example 25

1-(5-Benzyl-thiazol-2-yl)-4-methyl-piperazine

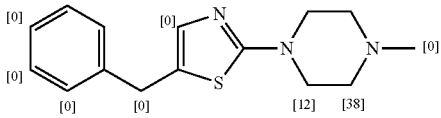 [SMILES: CN1CCN(c2ncc(Cc3ccccc3)s2)CC1]

The reaction was performed according to general method B:

0.18 mmol (50 mg) substrate, 0.004 mmol (5 mg) Shvo, 30 mmol (541 µL) $D_2O$, 6.5 mmol (500 µL) i-PrOH-$d_8$, 150° C., 18 h. Yield: 58%;

LC-MS (ESI) m/z (%): 274 (36) $[M_0+H]^+$, 275, (90), 276 (100), 277 (80), 278 (40), 279 (25), 360 (100), 280 (8), 281 (3).

$^1$H NMR (500 MHz, ACN-$d_3$): 2.23 (s, 3H), 2.38 (br m, 2.5H), 3.35 (br s, 3.5H), 3.97 (s, 2H), 6.90 (s, 1H), 7.23-7.30 ppm (m, 5H).

Optimization Experiments

Example 26

Into a microwave flask was placed 0.05 mmol (5 mol %, 5.4 mg) Shvo-catalyst and the flask was charged with argon. Then 0.1 mmol substrate, 200 µL toluene and 100 equiv. Deuterium-source (e.g. $D_2O$) was added. The reaction vessel was sealed and heated in a microwave (e.g. OEM Corporation: Discover SP) for 2 hours at 150° C. (dynamic mode, $T_{max}$ 150° C., $P_{max}$ 300 W, $p_{max}$ 17 bar, stirring: high). After cooling to room temperature the reaction mixture was analyzed by LC-MS.

a) In this experiment the influence of the deuterium source on the deuteration was investigated

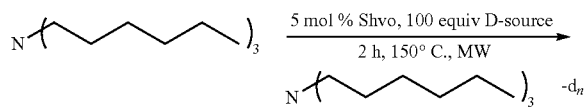

The results thereof are shown in Table 1.

TABLE 1

| Solvent | average D content [1] | LC-MS (ESI) m/z (%) |
|---|---|---|
| $D_2O$ (200 µL) | 9.4 | 270 (0) $[M_0 + H]^+$, 276 (1), 277 (5), 278 (14), 279 (25), 280 (28), 281 (19), 282 (7), 283 (1). |
| $CD_3OD$ (445 µL) | 10.7 | 270 (0) $[M_0 + H]^+$, 277 (1), 278 (2), 279 (8), 280 (21), 281 (36), 282 (28), 283 (5), 284 (1). |
| $CH_3OD$ (408 µL) | 10.1 | 270 (0) $[M_0 + H]^+$, 277 (1), 278 (7), 279 (17), 280 (26), 281 (30), 282 (16), 283 (2). |
| $CD_3OH$ (432 µL) | 0.7 | 270 (39) $[M_0 + H]^+$, 271 (37), 272 (18), 273 (5), 274 (1). |
| t-BuOD (942 µL) | 9.8 | 270 (0) $[M_0 + H]^+$, 276 (1), 277 (3), 278 (10), 279 (20), 280 (28), 281 (25), 282 (11), 283 (2). |
| i-PrOH-$d_8$ (764 µL) | 11.1 | 270 (0) $[M_0 + H]^+$, 278 (1), 279 (4), 280 (16), 281 (33), 282 (39), 283 (7), 284 (1). |
| i-PrOD (685 µL) | 4.4 | 270 (0) $[M_0 + H]^+$, 271 (3), 272 (9), 273 (18), 274 (23), 275 (22), 276 (15), 277 (8), 278 (3), 279 (1). |
| Acetone-$d_6$ (600 µL) | 3.2 | 270 (1) $[M_0 + H]^+$, 271 (8), 272 (18), 273 (25), 274 (22), 275 (17), 276 (6), 277 (2). |
| Cyclohexanone-$d_{10}$ (1080 mg) | 8.6 | 270 (0) $[M_0 + H]^+$, 275 (1), 276 (4), 277 (13), 278 (24), 279 (26), 280 (18), 281 (10), 282 (3), 283 (1). |
| Trifluoroacetic acid-d | 0 | 270 (83) $[M_0 + H]^+$, 271 (17). |

[1] Maximum 12

Example 27

In this experiment the effect of different D-source ratios of acetone-d6 and isopropanol-d8 was investigated

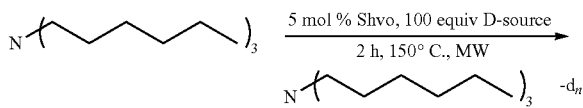

The results are shown in Table 2

TABLE 2

| Acetone-$d_6$ | i-PrOH-$d_8$ | average D content [1] | LC-MS (ESI) m/z (%) |
|---|---|---|---|
| 90 equiv. (594 µL) | 10 equiv. (77 µL) | 9.2 | 270 (0) $[M_0 + H]^+$, 275 (1), 276 (3), 277 (7), 278 (16), 279 (25), 280 (25), 281 (17), 282 (7), 28 (1). |
| 66 equiv. (436 µL) | 33 equiv. (252 µL) | 10.5 | 270 (0) $[M_0 + H]^+$, 277 (1), 278 (4), 279 (11), 280 (24), 281 (33), 282 (23), 283 (4). |
| 50 equiv. (330 µL) | 50 equiv. (384 ML) | 10.9 | 270 (0) $[M_0 + H]^+$, 278 (2), 279 (7), 280 (19), 281 (35), 282 (32), 283 (5), 284 (1). |
| 33 equiv. (218 µL) | 66 equiv. (505 ML) | 11.0 | 270 (0) $[M_0 + H]^+$, 278 (1), 279 (5), 280 (17), 281 (34), 282 (35), 283 (6), 284(1). |
| 10 equiv. (66 µL) | 90 equiv. (688 ML) | 10.6 | 270 (0) $[M_0 + H]^+$, 277 (1), 278 (3), 279 (10), 280 (23), 281 (35), 282 (25), 283 (4). |

[1] Maximum 12

The invention claimed is:

1. A process for preparing a deuterated compound (II) containing at least one structural element of the formula N—C—C, which is not part of an aromatic ring system, and wherein the amount of deuterium at the carbon atom in the alpha position and/or the carbon atom in the beta position of the structural element is at least 1%,
comprising reacting a compound (I) comprising a residue which contains at least one structural element N—C—C, wherein at least one H atom is at each carbon atom of the structural element and the N—C—C element is not part of an aromatic ring system,
with a deuterium source in the presence of a catalyst of formula (2)

1-UH-tetra-Z-cyclopentadienyl-(tetra-Z-2,4-cyclopentadien-1-U)-µ-hydro-tetra-L-diruthenium(II)     (2), wherein
UH is OH, NHR$_5$, or SH;
U is O, NR$_5$ or S;
R$_5$ is ($C_1$-$C_6$)alkyl, phenyl or —$CH_2$-phenyl;
Z is, independently of each other, ($C_1$-$C_6$)alkyl or phenyl, wherein each phenyl is optionally substituted by ($C_1$-$C_6$) alkyl or phenyl, wherein phenyl is optionally substituted 1 or more times by halogen, and
L is CO, CN or COD.

2. The process according to claim 1, wherein the structural element in a compound (I) is N—C(H)$_m$—C(H)$_n$ wherein m is 1 or 2 and n is 1, 2 or 3.

3. The process according to claim 1, wherein the structural element in a compound (I) is N—$CH_2$—$CH_2$.

4. The process according to claim 1, wherein the residue containing the structural element in compound (I) is —N($C_2$-$_{12}$)alkylene, —NH($C_2$-$C_{12}$)alkyl, —N(($C_1$-$C_{12}$)alkyl)(($C_2$-

$C_{12}$)alkyl), —($C_2$-$C_{12}$)alkylene-N(($C_1$-$C_{12}$)alkyl)$_2$, —($C_1$-$C_{12}$)alkylene-N(($C_1$-$C_{12}$)alkyl)(($C_2$-$C_{12}$)alkyl)) or ($C_3$-$C_{15}$)heterocycloalkyl.

5. The process according to claim 1, wherein compound (I) is a compound of formula (I)

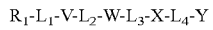

$$R_1\text{-}L_1\text{-}V\text{-}L_2\text{-}W\text{-}L_3\text{-}X\text{-}L_4\text{-}Y \qquad (I)$$

wherein
$R_1$ is
H,
OH,
C(O)—($C_1$-$C_6$)alkyl,
C(O)—V,
C(O)O$R_8$,
OC(O)—($C_1$-$C_6$)alkyl,
OC(O)NR7R8
OC(O)—V,
C(O)N$R_7R_8$,
Si—$R_7$,
OSi$R_7$,
$NR_7$—C(O)—($C_1$-$C_6$)alkyl,
$NR_7$—C(O)O($C_1$-$C_6$)alkyl,
$NR_7$—C(O)—V,
C(O)$_2R_8$,
$NR_7$—C(O)—N$R_7R_8$,
$NR_7R_8$,
S$R_8$,
S(O)—($C_1$-$C_6$)alkyl,
S(O)—V,
S(O)$_2NR_7R_8$,
$NR_7$—SO$_2$—($C_1$-$C_6$)alkyl,
$NR_7$—SO$_2$—($C_1$-$C_6$)alkylene-V,
NR7—SO$_2$—V,
S(O)$_2$—($C_1$-$C_6$)alkyl,
S(O)$_2$—O$R_8$, or
OS(O)$_2$—$R_8$;
$R_7$ is H, ($C_1$-$C_{12}$)alkyl, or phenyl;
$R_8$ is H, ($C_1$-$C_{12}$)alkyl;
$L_1$ is
a bond,
($C_1$-$C_{12}$)alkylene,
($C_1$-$C_6$)alkenylene, or
($C_2$-$C_6$)alkynylene;
$L_2$, $L_3$, or $L_4$ is independently of each other a group $R_2$—$R_3$—$R_4$ wherein
$R_2$ and $R_4$ are independently of each other selected from
a bond,
O,
C(O),
C(O)CO,
C(O)N$R_7$,
$NR_7$C(O),
N(C(O)R7),
C(O)O,
OC(O),
$NR_7$,
S,
S(O),
S(O)$_2$,
S(O)$_2$—O,
OS(O)$_2$,
S(O)$_2NR_7$, or
$NR_7$S(O)$_2$;
$R_3$ is
a bond,
($C_1$-$C_{12}$)alkylene,
($C_1$-$C_6$)alkenylene, or
($C_2$-$C_6$)alkynylene;
with the proviso that $R_2$ or $R_4$ is a bond if $R_3$ is a bond;
V, W, X and Y are
a bond,
($C_3$-$C_8$)cycloalkyl,
($C_5$-$C_{15}$)heteroaryl,
($C_6$-$C_{10}$)aryl, or
($C_3$-$C_{15}$)heterocycloalkyl,
wherein said ($C_6$-$C_{10}$)aryl, ($C_5$-$C_{14}$)heteroaryl, ($C_3$-$C_{15}$)heterocycloalkyl or ($C_3$-$C_8$)cycloalkyl is optionally substituted one, two, three or four times by a group independently of each other selected from $R_9$;
and wherein Y may also be H,
$R_9$ is
halogen,
oxo,
OH,
NO$_2$,
CN,
SO$_2$—N=CH—N[($C_1$-$C_6$)alkyl]$_2$,
SF$_5$,
CF$_3$,
C(NH)(NH$_2$),
PO$_3(R_7)_{1-3}$,
$R_1$,
$L_1$-$R_1$,
O-$L_1$-$R_1$,
V,
L1-V, or
O-$L_1$-V;
and a V substituent in $R_9$ may not be further substituted by a V substituent;
wherein in any alkyl or alkylene residue one or more carbon atoms are optionally replaced by O, provided that two oxygens are not directly connected to each other, and wherein any alkyl or alkylene is optionally substituted by one, two or three residues independently of each other selected from
halogen, cyano, hydroxyl, O($C_1$-$C_6$)Alkyl, S($C_1$-$C_6$)alkyl, phenyl, O-phenyl, benzyl, OC(O)($C_1$-$C_6$)alkyl, C(O)($C_1$-$C_6$)alkyl, C(O)O($C_1$-$C_6$)alkyl or C(O)OH.

6. The process according to claim 5, wherein $R_1$ is $NR_7R_8$.

7. The process according to claim 5, wherein $R_7$ and $R_8$ are ($C_1$-$C_{12}$)alkyl.

8. The process according to claim 5, wherein $L_1$ is a bond or ($C_1$-$C_6$)alkylene.

9. The process according to claim 5, wherein $R_1$-$L_1$ is ($C_1$-$C_{12}$)alkyl.

10. The process according to claim 5, wherein one or more of V, W, X or Y contains the structural element N—C—C.

11. The process according to claim 10, wherein one or more of V, W, X or Y is ($C_3$-$C_{15}$)heterocycloalkyl.

12. The process according to claims 10, wherein one or more of V, W, X or Y is, independently of each other, selected from

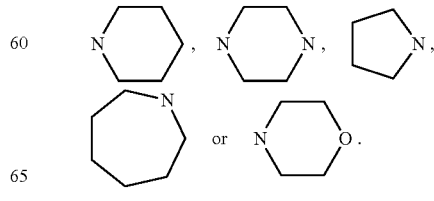

13. The process according to claim 5, wherein $R_2$ is a bond, O, CO, C(O)O, NH, N(C(O)R$_7$), C(O)NH or NHC(O).

14. The process according to claim 5, wherein $R_3$ is a bond, $(C_1-C_6)$alkenylene or $(C_1-C_6)$alkylene optionally substituted, independently of each other, one, two or three times by OH, halogen, C(O)O$(C_1-C_6)$alkyl, OC(O)$(C_1-C_6)$alkyl or optionally substituted phenyl.

15. The process according to claim 5, wherein $R_4$ is a bond, O, C(O), C(O)O, OC(O), S(O)$_2$, NH, NHC(O) or C(O)NH.

16. The process according to claim 5, wherein
R1 is H, OH or NR$_7$R$_8$;
L1 is a bond or $(C_1-C_6)$alkylene;
V is a bond, $(C_6-C_{10})$aryl preferably phenyl, $(C_3-C_8)$cycloalkyl, $(C_5-C_{15})$heteroaryl or $(C_3-C_{15})$heterocycloalkyl, preferably

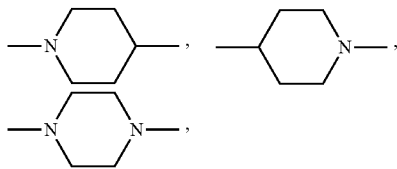

each of L2, L3 and L4 is R2-R3-R4, wherein
R2 is a bond, O, S(O)2, C(O), C(O)O, OC(O), NH, NHC(O), N(C(O)R$_7$) or C(O)NH;
R3 is a bond, (C1-C6)alkenylene or $(C_1-C_6)$alkylene optionally substituted one, two or three times by a group selected from $(C_1-C_6)$alkyl, C(O)—$(C_1-C_6)$alkyl, OH, OC(O)—$(C_1-C_6)$alkyl, or $(C_6-C_{10})$aryl preferably phenyl, wherein $(C_6-C_{10})$aryl is optionally substituted one, two three times by R9;
R4 is a bond, O, S(O)$_2$, NH, NHC(O), C(O)NH, C(O) or C(O)O, provided that R2 or R4 is a bond if R3 is a bond;
W and X is, independently of each other, a bond, $(C_6-C_{10})$aryl preferably phenyl, $(C_3-C_8)$cycloalkyl, $(C_5-C_{15})$heteroaryl or $(C_3-C_{15})$heterocycloalkyl, and
Y is H, $(C_6-C_{10})$aryl preferably phenyl, $(C_3-C_8)$cycloalkyl, $(C_5-C_{15})$heteroaryl or $(C_3-C_{15})$heterocycloalkyl;
and any $(C_1-C_6)$alkylene in L1 and R3 is optionally substituted one, two or three times by a group selected from halogen, $(C_1-C_6)$alkyl, C(O)—$(C_1-C_6)$alkyl, C(O)O $(C_1-C_6)$alkyl, OH, OC(O)—$(C_1-C_6)$alkyl, or phenyl, and/or one or more carbon atoms are optionally replaced by O;
and in L1, R3, V, W, X and Y any $(C_6-C_{10})$aryl, $(C_5-C_{15})$heteroaryl or $(C_3-C_{15})$heterocycloalkyl is optionally substituted one, two, or three times by R9.

17. The process according to claim 1, wherein the catalyst is 1-Hydroxy-tetraphenylcyclopentadienyl-(tetraphenyl-2,4-cyclopentadien-1-one)-μ-hydrotetracarbonyldiruthenium (II).

18. The process according to claim 1, wherein the catalyst is used in an amount of 1 to 50 mol %.

19. The process according to claim 1, wherein the amount of deuterium at each carbon atom in the N—C—C structural element is at least 10%.

* * * * *